US007601846B2

(12) United States Patent
Cottam et al.

(10) Patent No.: US 7,601,846 B2
(45) Date of Patent: Oct. 13, 2009

(54) COMPOUNDS HAVING ACTIVITY AS INHIBITORS OF APOPTOSIS

(75) Inventors: Howard B. Cottam, Escondido, CA (US); Dennis A. Carson, La Jolla, CA (US); Sylvie Barchechath, Geneva (CH)

(73) Assignee: The Regents of the University of California, Oakland, CA (US)

( * ) Notice: Subject to any disclaimer, the term of this patent is extended or adjusted under 35 U.S.C. 154(b) by 549 days.

(21) Appl. No.: 11/271,511

(22) Filed: Nov. 10, 2005

(65) Prior Publication Data

US 2006/0122178 A1    Jun. 8, 2006

Related U.S. Application Data

(63) Continuation-in-part of application No. 11/077,986, filed on Mar. 11, 2005, now abandoned, which is a continuation of application No. 10/364,663, filed on Feb. 11, 2003, now abandoned, which is a continuation of application No. PCT/US01/25175, filed on Aug. 10, 2001.

(60) Provisional application No. 60/301,340, filed on Jun. 26, 2001.

(51) Int. Cl.
    *C07D 513/04*    (2006.01)
    *A61K 31/429*    (2006.01)
(52) U.S. Cl. .................. 548/151; 544/133; 546/199; 514/233.2; 514/322; 514/366
(58) Field of Classification Search ............ 548/151; 546/199; 544/133; 514/322, 233.2, 366
    See application file for complete search history.

(56) References Cited

U.S. PATENT DOCUMENTS

| 3,843,681 | A |   | 10/1974 | Demerson et al. |
|---|---|---|---|---|
| 4,020,062 | A |   | 4/1977 | Hardtmann |
| 4,337,760 | A |   | 7/1982 | Rubin |
| 4,497,817 | A | * | 2/1985 | Murase et al. .............. 548/150 |
| 4,537,889 | A |   | 8/1985 | Spitzer |
| 4,559,157 | A |   | 12/1985 | Smith et al. |
| 4,567,263 | A |   | 1/1986 | Eicken et al. |
| 4,608,392 | A |   | 8/1986 | Jacquet et al. |
| 4,762,705 | A |   | 8/1988 | Rubin |
| 4,820,508 | A |   | 4/1989 | Wortzman |
| 4,938,949 | A |   | 7/1990 | Borch et al. |
| 4,992,478 | A |   | 2/1991 | Geria |
| 5,561,151 | A |   | 10/1996 | Young et al. |
| 5,696,260 | A |   | 12/1997 | Shaw et al. |
| 5,811,558 | A |   | 9/1998 | Adger et al. |
| 5,939,455 | A |   | 8/1999 | Rephaeli |
| 5,955,504 | A |   | 9/1999 | Wechter et al. |
| 6,066,741 | A |   | 5/2000 | Vigano' et al. |
| 6,110,955 | A |   | 8/2000 | Nudelman et al. |
| 6,160,018 | A |   | 12/2000 | Wechter et al. |
| 6,545,034 | B1 |   | 4/2003 | Carson et al. |

2006/0040934 A1    2/2006    Cottam et al.

FOREIGN PATENT DOCUMENTS

| DE | 2226340 | 3/1973 |
|---|---|---|
| EP | 289262 A2 | 11/1988 |
| JP | 11029475 | 2/1999 |
| JP | 11-106340 | 4/1999 |
| JP | 1110630 | 4/1999 |
| WO | WO-9628148 A2 | 9/1996 |
| WO | WO-9742192 A1 | 11/1997 |
| WO | WO-9809603 A2 | 3/1998 |
| WO | WO-9818490 A1 | 5/1998 |
| WO | WO-9916790 A1 | 4/1999 |
| WO | WO-9941985 A1 | 8/1999 |
| WO | WO-9947643 A1 | 9/1999 |
| WO | WO-0013410 A1 | 3/2000 |
| WO | WO-0044364 A2 | 8/2000 |

OTHER PUBLICATIONS

In: *Remington's Pharmaceutical Sciences, Eighteenth Edition*, Gennaro, A.R., (ed.), Mack Publishing Company, Easton, PA,(1990),pp. 1115-1122.

*The Merck Index, Thirteenth Edition*, Budavari, S., et al., (eds.), Merck & Co., Inc., Rahway, N.J., "Etodolac, Entry No. 3905 ",(1990),p. 685.

*Drug Facts and Comparisons, 1995 Edition*, Wolters Kluwer Co.,(1995),2775-2789.

Abramson, S. B., et al., "The Mechanisms of Action of Nonsteroidal Antiinflammatory Drugs", *Arthritis & Rheumatism*, 32 (1), (Jan. 1989),1-9.

Akimoto, Toshihiko , "Abrogation of Bronchial Eosinophilic Inflamation and Airway Hyperreactivity in Signal Transducers and Activators of Transcription (STAT)6-deficient Mice", *Journal of Experimental Medicine*, 187(9), (1998),1537-1542.

Alexanian, R. , et al., "The Treatment of Multiple Myeloma", *The New England Journal of Medicine*, 330 (7), (Feb. 17, 1994),484-489.

Andreani, A. , et al., "6-Pyridinylimidazo [2,1-b] thizoles and thizolines as potential cardiotonic agents", *Eur. j. Med. Chem.*, 20(1), (1986),pp. 93-94.

Andreani, A. , et al., "In-vivo cardiotonic activity of aryl- and pyridyl-substituted fused imidazoles", *Arzneim.-Forsch.*, 48 (3), (1998),pp. 232-235.

Andreani, A., "Potential antitumor agents, VII, 5-substituted 6-phenylimidazo[2,1-b]thizoles", *Arch. Pharm.*, 315, (1982),pp. 451-456.

Andreani, A. , et al., "Potential Antitumor Agents. 24. Synthesis and Pharmacological Behaviour of Imidazo[2,1-b]thiazole Guanylhydrazones Bearing at Least One Chlorine", *J.Med.Chem.*, 39(14), (1996),pp. 2852-2855.

(Continued)

*Primary Examiner*—Bernard Dentz
(74) *Attorney, Agent, or Firm*—Schwegman, Lundberg & Woessner, P.A.

(57) ABSTRACT

The present invention provides compounds that can protect mammalian cells from the damaging effects of chemotherapy, irradiation, or in other situations in which it is desirable to protect tissue from the consequences of clinical or environmental stress.

4 Claims, 8 Drawing Sheets

OTHER PUBLICATIONS

Andreani, A., et al., "Potential antitumor agents. VIII. Allyl propargyl and cyanomethyl esters of imidazo[2,1-b]thiazole-5-carboxylic acids", *Arch.Pharm.*, 316(2), (1983),pp. 141-146.

Andreani, A., et al., "Substituted 6-phenylimidazol[2,1-b]thiazoles and thiazolines as potential cardiotonic agents", *Eur.J.Med.Chem.*, 19(3), (1984),pp. 219-222.

Andreani, A., et al., "Synthesis and cardiotonic activity of aryl-or pyridyl-substituted fused imidazoles", *Eur.J.Med.Chem*, 29(5), (1994),pp. 339-342.

Andreani, A., et al., "Synthesis and cardiotonic activity of methylthiophenylimidazo{2,1-b]thiazoles and thiazolines", *Eur.J.Med.Chem.*, 21(1), (1986),pp. 55-58.

Andreani, A., et al., "Synthesis of 6-substituted formylimidazo[2,1-b] thiazoles", *Bolletino Chimico Farmaceutico*, 118 (11), (1979),pp. 694-698.

Andreani, A., et al., "Synthesis of imidazo[2,1-b]thiazoles as herbicides", *Pharm.Acta Helv.*, 71(4), (1996),pp. 247-252.

Andreani, A., et al., "Thienylimidazo[2,1-b]thiazoles as inhibitors of mitochondrial NADH Dehydrogenase", *J.Med.Chem.*, 38(7), (1995),pp. 1090-1097.

Armianianskii, (1990),245-262.

Barlogie, B, "Prognostic Factors with High-Dose Melphalan for Refractory Multiple Myeloma.", *Blood*, 72(6), (Dec. 1988),2015-2019.

Bataille, R, et al., "Multiple Myeloma", *New England Journal of Medicine*, 336, (1997),1657-1664.

Becker-Scharfenkamp, U., et al., "Evaluation of the Stereoselective Metabolism of the Chiral Analgesic Drug Etodolac by High-Performance Liquid Chromatography", *Journal of Chromatography*, 621 (2), (Nov. 24, 1993),pp. 199-207.

Bellosillo, Beatriz, et al., "Aspirin and Salicylate Induce Apoptosis and Activation of Caspases in B-Cell Chronic Lymphocytic Leukemia Cells", *Blood*, 92 (4), (Aug. 15, 1998),1406-1414.

Berendes, U., et al., "Simultaneous Determination of the Phase II Metabolites of the Non Steriodal Anti-inflammatory Drug Etodolac in Human Urine", *Enantiomer*, 1, Abstract Only, Chemical Abstracts, Abstract No. 126:207064q,(1996),415-422.

Brenna, E., et al., "New Enzymatic and Chemical Approaches to Enantiopure Etodolac", *Tetrahedron*, 53, (1997),17769-17780.

Brocks, D. R., et al., "Etodolac Clinical Pharmacokinetics", *Clinical Pharmacokinetics*, 26 (4), (1994),pp. 259-274.

Burnett, J. C., et al., "Atrial Natriutetic Peptide Elevation in Congestive Heart Failure in the Human", *Science*, 231, (Mar. 7, 1986),1145-1147.

Burnett, J. C., et al., "Effects of synthetic atrial natriuretic factor on renal function and renin release", *American Journal of Physiology: Renal, Fluid and Electrolyte Physiology*, 16(5), (Nov. 1984),pp. F863-F866.

Carson, D. A., et al., "Oral Antilymphocyte Activity and Induction of Apoptosis by 2-chloro-2'-arabino-fluoro-2'-deoxyadenosine", *Proceedings of the National Academy of Sciences USA*, 89 (7), (Apr. 1, 1992),2970-2974.

Chinetti, G., et al., "Activation of Proliferator-activated Receptors alpha and γ Induces Apoptosis of Human Monocyte-derived Macrophages", *Journal of Biological Chemistry*, 273 (40), (Oct. 2, 1998),25573-25580.

Coppola, Gary M., "Chemisrty of 2H-3, 1-Benzoxazine-2, 4(1H)-dione (Isatoic Anhydride). 2. Reactions with Thiopseudoreas and Carbanions", *Journal of Organic Chemistry*, (1976),825-831.

Cordon-Cardo, C., et al., "Genetic Studies and Molecular Markers of Bladder Cancer", *Seminars in Surgical Oncology*, 13 (5), (1997),pp. 319-327.

Cunningham, D, et al., "High-dose Melphalan for Multiple Myeloma: Long-term Follow-up Data", *Journal of Clinical Oncology*, 12, (1994),764-768.

Dancescu, M, "Interleukin 4 Protects Chronic Lymphocytic Leukemic B Cells from Death by Apoptosis and Upregulates BcI-2 Expression", *J. Exp. Med.*, (1992),1319-1326.

Demerson, C. A., et al., "Etodolic Acid and Related Compounds. Chemistry and Antiinflammatory Actions of Some Potent Di- and Trisubstituted 1,3,4,9-Tetrahydropyrano[3,4-b]indole-1-acetic Acids", *Journal of Medicinal Chemistry*, 19 (3), (1976),pp. 391-395.

Demerson, C. A., et al., "Resolution of Etodolac and Antiinflammatory and Prostaglandin Synthetase Inhibiting Properties of the Enantiomers", *J. Med. Chem.*, 26 (12), (Dec. 1983),pp. 1778-1780.

Donehower, L. A., et al., "Mice Deficient For p53 Are Developmentally Normal But Susceptible to Spontaneous Tumours", *Nature*, 356, (Mar. 19, 1992),pp. 215-221.

Drachenberg, D. E., "Treatment of Prostate Cancer: Watchful Waiting, Radical Prostatectomy, and Cryoablation", *Seminars in Surgical Oncology*, 18 (1), (Jan./Feb. 2000),pp. 37-44.

Duffy, C. P., et al., "Enhancement of Chemotherapeutic Drug Toxicity to Human Tumour Cells In Vitro by a Subset of Non-Steroidal Anti-Inflammatory Drugs (NSAIDs)", *European Journal of Cancer*, 34 (8), (Jul. 1998),pp. 1250-1259.

Ermolaeva, V. G., et al., "Synthesis and Tuberculostatic Activity of Certain Heterocyclic Substituted Arylthioureas", *Translated from: Khimiko-Farmatsaevticheskii Zhurnal, No. 1*, Original article submitted Jun. 16, 1966.,(Jan. 1967),pp. 17-19.

Francis, John E., "Anxiolytic Properties of Certain Annelated [1,2,4] Triazolo [1,5-c] pyrimidin-5 (6-H)-ones", *Journal of Medicinal Chemistry*, (1991),2899-2906.

Gineinah, Magdy M., et al., "Synthesis and antiinflammatory evaluationof new 2- and 3-substituted 1,2,4-triazolo[4,3-c] and [1,5-c]quinazoline derivatives", *Med. Chem. Res.*, 10 (4) No. 134222676, (2000),243-252.

Gottlieb, T. M., et al., "p53 in Growth Conrtol and Neoplasia", *Biochimica et Biophisica Acta*, 1287, (1996),pp. 77-102.

Gueiffier, A, "Heterocyclic Compounds with a Bridgehead Nitrogen Atom. Synthesis in the Imidazo[1,2-c] quinazoline series", *Journal of Heterocyclic Chemistry*, (1990),421-425.

Hahnfeld, L. E., et al., "Prostate Cancer", *The Medical Clinics of North America—The Aging Male Patient*, 83 (5), (Sep. 1999),pp. 1231-1245.

Harousseau, J. L., et al., "Double-Intensive Therapy in High-Risk Multiple Myeloma", *Blood*, 79 (11), (Jun. 1, 1992),pp. 2827-2833.

Heckendorn, Roland, et al., "Synthese von [1,2,4] Triazolo [1,5-a] chinazolinen", *Helvetica Chimica Acta*, vol. 63,(1980),1-9.

Heim, Markus H., "The Jak-Stat Pathway: Cytokine Signalling from the Receptor to the Nucleus", *Journal of Receptor and Signal Transduction Research*, (1999),75-120.

Hendry, J. H., et al., "P53 deficiency produces fewer regenerating spermatogenic tubules after irradiation", *Int. J. Radiat. Biol.*, 70 (6), (1996),pp. 677-682.

Hu, Ming K., et al., "Guanidine-annelated heterocycles XIII", *Database Registry file on STN* (Columbus, OH) No. 115-71526.

Ihle, James N., "Jaks and Stats in Cytokine Signaling", *Stem Cells*, (1997),105-112.

Jacks, T., et al., "Tumor Spectrum Analysis in p53-Mutant Mice", *Current Biology*, 4 (1), (1994),pp. 1-7.

Kapp, Ursala, "Interleukin 13 is Secreted by and Stimulates the Growth of Hodgkin and Reed-Sternberg Cells", *J. Exp. Med.*, (1999),1939-1945.

Kawakami, Koji, "Structure, Function, and Targeting of Interleukin 4 Receptors on Human Head and Neck Cancer Cells", *Cancer Research*, (2000),2981-2987.

Komarov, P. G., et al., "A Chemical Inhibitor of p53 That Protects Mice from the Side Effects of Cancer Therapy", *Science*, 285, (Sep. 10, 1999),pp. 1733-1737.

Komarova, E. A., et al., "Could p53 be a target for therapeutic suppression?", *Seminars in Cancer Biology*, 8 (5), Article No. se980101,(1998),pp. 389-400.

Komarova, E. A., et al., "Transgenic mice with p53-responsive lacZ: p53 activity varies dramatically during normal development and determines radiation and drug sensitivity in vivo", *The EMBO Journal*, 16 (6), (1997),pp. 1391-1400.

Krajewski, S., et al., "Detection of Multiple Antigens on Western Blots", *Analytical Biochemistry*, 236 (2), Article No. 0160,(May 1996),pp. 221-228.

Landis, S. H., et al., "Cancer Statistics, 1998", *CA Cancer J. Clin.*, 48(1), (1998),pp. 6-29.

Lee, D. H., "Proteasome Inhibitors: Valuable New Tools For Cell Biologists", *Trends in Cell Biology*, 8, (Oct. 1998),pp. 397-403.

Lehmann, J. M., et al., "Peroxisome Proliferator-activated Receptors alpha and Y Are Activated by Indomethacin and Other Non-steroidal Anti-inflammatory Drugs", *Journal of Biological Chemistry*, 272 (6), (Feb. 7, 1997),3406-3410.

Leman, Eddy S., et al., "Characterization of the Nuclear Matrix Proteins in a Transgenic Mouse Model for Prostate Cancer", *Journal of Cellular Biochemistry*, 86, (2002),203-212.

Leoni, L. M., et al., "Induction of an Apoptotic Program in Cell-Free Extracts by 2-Chloro-2'-deoxyadenosine 5'-triphosphate and Cytochrome C", *PNAS*, USA, 95 (16), (Aug. 4, 1998),pp. 9567-9571.

Levine, A. J., et al., "The 1993 Walter Hubert Lecture: The role of the p53 tumour-suppressor gene in tumorigenesis", *British Journal of Cancer*, 69 (3), (1994),pp. 409-416.

Likhale, M A., et al., *J. Ind. Chem. Soc.*, 69, (1992),667.

Likhate, M A., "Triazoloquinazolines Part-3 Synthesis and Biological Acitivity of some 2-Aryl-3-acetyl, 3-dihydrotriazoloquinazolines", *J. Indian Chem. Soc.*, (1992),667-668.

Liu, Kathleen D., "JAK/STAT Signaling by Cytokine Receptors", *Current Opinion in Immunology*, (1998),271-278.

Lochmuller, C. H., et al., "Chromatographic Resolution of Enantiomers—Selective Review", *Journal of Chromatography*, 113 (3), (Oct. 22, 1975),283-302.

Martel, R. R., et al., "Anti-inflammatory and Analgesic Properties of Etodolic Acid in Rats", *Canadian Journal of Physiology and Pharmacology*, 54 (3), (Jun. 1976),pp. 245-248.

Mooney, P. T., et al., "Cell Pathways' Exisulind 'Aptosyn' Demonstrates Potential to Delay Hormone Therapy in Post-Prostatectomy Men at Risk of Prostate Cancer Recurrence", http://biz.yahoo.com/bw/000501/ga_cell_pa_1.html, (May 2000),3 p.

Muller-Ladner, Ulf, "Activation of the IL-4 STAT Pathway in Rheumatoid", *The Journal of Immunology*, (2000),3894-3901.

Nardella, Francis A., et al., "Enhanced Clearance of Leukemic Lymphocytes in B Cell Chronic Lymphocytic Leukemia (CLL) with Etodolac", *Arthritis & Rheumatism*, 42 (9) Supplement, Abstract No. 41, (Sep. 1999),p. S56.

Ostrand-Rosenberg, Suzanne, "Cutting Edge: STAT6-Deficient Mice Have Enhanced Tumor Immunity to Primary and Metastatic Mammary Carcinoma", *The Journal of Immunology*, (2000),6015-6019.

Potts, K T., "1,2,4-Triazoles. XXIV. Isomerization of s-Triazolo[4,3-c]quinazoline Derivatives", *J. Org. Chem.*, (1970),3448-3451.

Ricote, M., et al., "The Peroxisome Proliferator-Activated Receptor-Y is a Negative Regulator of Macrophage Activation", *Nature*, 391, (Jan. 1, 1998),pp. 79-82.

Riedel, D. A., et al., "The Epidemiology of Multiple Myeloma", *Hematology/Oncology Clinics of North America, Multiple Myeloma*, 6 (2), (Apr. 1992),pp. 225-247.

Rogel, A., et al., "p53 Cellular Tumor Antigen: Analysis of mRNA Levels in Normal Adult tissues, Embryos, and Tumors", *Molecular and Cellular Biology*, 5 (10), (1985),pp. 2851-2855.

Royall, J. A., et al., "Evaluation of 2',7'-Dichlorofluorescin and Dihydrorhodamine 123 as Fluorescent Probes for Intracellular H2O2 in Cultured Endothelial Cells", *Archives of Biochemistry and Biophysics*, 302 (2), (May 1, 1993),pp. 348-355.

Schmid, P., et al., "Expression of p53 during mouse embryogenesis", *Development*, 113 (3), (Nov. 1991),pp. 857-865.

Schwartz, D., et al., "Expression of p53 Protein in Spermatogenesis is Confined to the Tetraploid Pachytene Primary Spermatocytes", *Oncogene*, 8 (6), (Jun. 1993),pp. 1487-1494.

Shiff, S. J., et al., "Nonsteroidal Antiinflammatory Drugs Inhibit the Proliferation of Colon Adenocarcinoma Cells: Effects on Cell Cycle and Apoptosis", *Experimental Cell Research*, 222, Article No. 0023, (1996),pp. 179-188.

Singh, A., et al., "Heterocyclic Systems Containing Bridgehead Nitrogen Atom: Part XXV—Syntheses of Imidazo [2,1-b] benzothiazoles & Quinxalino-[2,3:4',5']imidazo[2',1'-b]benzothiazoles", *Indian Journal of Chemistry*, 14B (7), (Dec. 1976),pp. 997-998.

Soldabols, I, et al., *Khim. Pharm. Zh.*, (1967).

Steele, R.J.C., et al., "The p53 Tumour Suppressor Gene", *British Journal of Surgery*, 85 (11), (1998),pp. 1460-1467.

Takeda, Kiyoshi, et al., "Essential Role of STAT6 in IL-4 Signalling", *Nature*, (1996),627-630.

Tang, D. G., et al., "Target to Apoptosis: A Hopeful Weapon for Prostate Cancer", *The Prostate*, (1997),pp. 284-293.

Terabe, Masaki, "NKT Cell-Mediated Repression of Tumor Immunosurveillance by IL-13 and the IL-4R-STAT6 Pathway", *Nature Immunology*, (2000),515-520.

Tron, V. A., et al., "p53-Regulated Apoptosis Is Differentiation Dependent in Ultraviolet B-Irradiated Mouse Keratinocytes", *American Journal of Pathology*, 153 (2), (Aug. 1998),pp. 579-585.

Van Breemen, R. B., et al., "Characterization of Oxygen-Linked Glucuronides by Laser Desorption Mass Spectrometry", *Biomed. Mass Spectrom.*, 11, Abstract Only, Chemical Abstracts, Abstract No. 101:106777c,(1984),278-283.

Venuti, M. C., et al., "Synthesis and Biological Evaluation of omega-(N,N,N- trialkylammonium)alkyl Esters and Thioesters of Carboxylic Acid Nonsteroidal Antiinflammatory Agents", *Pharm. Res.*, 6, Abstract Only, Chemical Abstracts, Abstract No. 112:111681y,(1989),867-873.

Wang, X., et al., "Antipoptotic Action of 1,25-Dihydroxyvitamin D3 Is Associated with Increased Mitochondrial MCL-1 and RAF-1 Proteins and Reduced Release of Cytochrome c", *Experimental Cell Research*, 235 (1), Article No. EX973667,(1997),pp. 210-217.

Wechter, W. J., et al., "E-7869 (R-Flurbiprofen) Inhibits Progression of Prostate Cancer in the Tramp Mouse", *Cancer Research*, 60, (Apr. 15, 2000),pp. 2203-2208.

Weiss, H. A., et al., "Aspirin, Non-Steroidal Anti-Inflammatory Drugs and Protection from Colorectal Cancer: a Review of the Epidemiological Evidence", *Scandinavian Journal of Gastroenterology*, 31 (Suppl. 220), (1996),pp. 137-141.

Wilen, S. H., et al., "Strategies In Optical Resolutions", *Tetrahedron*, 33 (21), Tetrahedron Report No. 38,(1977),pp. 2725-2736.

* cited by examiner

110
C15H13BrCl2N2S
MOL. WT.: 404.15

99
C15H15BrF2N2OS
MOL. WT.: 389.26

105
C15H14BrClN2S
MOL. WT.: 369.71

101
C15H16BrClN2OS
MOL. WT.: 387.72

C22H19BrN2O2S
MOL. WT.: 455.37

93

109
C15H15BrN2OS
MOL. WT.: 351.26

104

C₁₅H₁₄BrFN₂S
MOL. WT.: 353.25

130

C₁₆H₁₅BrN₂OS
MOL. WT.: 363.27

100

C₁₅H₁₆BrFN₂OS
MOL. WT.: 371.27

4

C₁₆H₁₃BrN₂S
MOL. WT.: 345.26

103

C₁₅H₁₃BrF₂N₂S
MOL. WT.: 371.24

108

C₁₅H₁₅BrCl₂N₂OS
MOL. WT.: 422.17

107

$C_{17}H_{20}BrClN_2OS$
MOL. WT.: 415.78

111

$C_{16}H_{16}Br_2N_2S$
MOL. WT.: 428.19

140

$C_{15}H_{16}Br_2N_2OS$
MOL. WT.: 432.17

COMPOUNDS HAVING ACTIVITY AS INHIBITORS OF APOPTOSIS

CROSS-REFERENCE TO RELATED APPLICATIONS

This application is a continuation-in-part of U.S. patent application Ser. No. 11/077,986, filed Mar. 11, 2005 now abandoned, which is a continuation application of U.S. patent application Ser. No. 10/364,663, filed Feb. 11, 2003 now abandoned, which application is a continuation under 35 U.S.C. 111(a) of PCT/US01/25175, filed Aug. 10, 2001, which claims priority to U.S. patent application Ser. No. 09/637,531, filed Aug. 11, 2000, and U.S. Provisional Patent Application Ser. No. 60/301,340, filed Jun. 26, 2001, all of which are incorporated by reference herein.

GOVERNMENT FUNDING

This invention was made with the assistance of the National Institutes of Health under Grant Nos. GM23200 and CA81534. The U.S. Government has certain rights in this invention.

BACKGROUND OF THE INVENTION

The prevention of undesired cell death has become an important goal for pharmacologic intervention in a variety of clinical settings. Profound disability can result from apoptotic cell death and tissue injury due to ischemia, chemotherapeutic agents, ionizing radiation, or hyperthermia. Recently, a small molecule, 2-(2-imino-4,5,6,7-tetrahydro-benzothiazol-3-yl)-1-p-tolyl-ethanone hydrobromide (PFT-α; 1),

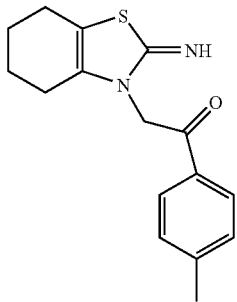

was originally identified from a broad screen of 10,000 compounds to inhibit cell death from gamma radiation, Komarov, P. G.; et al., *Science* 1999, 285, 1733-1737. In addition, Komarov's results indicated that this compound was shown to protect mice from lethal genotoxic stress. In addition, it was discovered that PFT-α was also shown to protect focal cortical ischemic injury and neuronal excitotoxic damage, Culmsee, C., et al., *J. Neurochem.* 2001, 77, 220-228, and Culmsee, C. et al., *Brain Res Mol Brain Res.* 2001, 87, 257-262. The protection provided by PFT-α was attributed to inhibition of p53 transactivation. Supporting evidence has included diminished nuclear accumulation with decreased p53 DNA binding activity, decreased caspase activity and suppression of mitochondrial dysfunction. Furthermore, the transcription of apoptosis-associated gene products p53, Bax and p21 was inhibited, Proietti De Santis, L., et al., *DNA Repair* 2003, 2, 891-900.

However, the activity of PFT-α is not limited to inhibiting the transactivation of p53. This small molecule has been found to also suppress the heat shock and glucocorticoid signaling pathways Komarova, E. A., et al., *J Biol Chem.* 2003, 278, 15465-15468. Glucocorticoid-induced cell death is independent of p53 Clarke, A. R., et al., *Nature* 1993, 362, 849-852. This pathway, however, also induces the transcription and activity of the proapoptotic BH3 (Bcl-2 Homology)-only protein p53-upregulated modulator of apoptosis (PUMA) Han, J.-W.; Flemington, C. et al., *Proc Natl Acad Sci USA.* 2001, 98, 11318-11323. When this death-inducing signal reaches the mitochondria, a series of cell-death related events ensues. The inner mitochondrial membrane loses its potential and cytochrome c is released into the cytoplasm, where it can associate with ATP, apoptosis-activating factor-1, and procaspase-9. This apoptosome complex cleaves procaspase-9 to caspase-9, which in turn cleaves procaspase-3, initiating the cascade of protease activation in the execution phase of apoptosis Li, P., et al., *Cell* 1997, 91, 479-489. and Zou, H., et al., *Cell* 1997, 90, 405-413.

PFT-α has been reported to diminish p53-dependent and independent mitochondria mediated cell death in vitro and in vivo, Komarov, P. G.; et al., *Science* 1999, 285, 1733-1737 and Komarova, E. A., et al., *J Biol Chem.* 2003, 278, 15465-15468. The multiplicity of molecular pathways that are reportedly influenced by PFT-α suggests that the cytoprotective effect could be further optimized. Furthermore, PFT-α is not stable under physiologic conditions and spontaneously undergoes ring closure to form the imidazo[2,1-b]benzothiazole (IBT) 2, Singh, A.; Mohan, J., et al., *Indian J. Chem., Sect. B* 1976, 14B, 997-998.

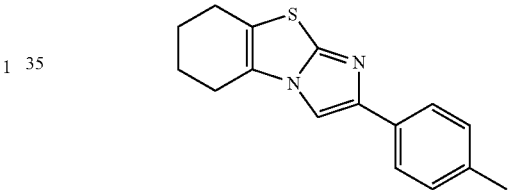

In spite of recent reports by Zhu, X., et al., *J Med Chem.* 2002, 45, 5090-5097, and Pietrancosta, N., et al., *Bioorg Med Chem Lett.* 2005, 15, 1561-1564, describing a few of the compounds prepared here, the biologically active form of PFT-α (open versus closed ring) has not previously been formally determined. Elucidation of the active ring structure would allow investigation of further chemical modifications that may enhance the potency of the compound. In addition, alternative ring structures, such as the quaternary salts recently reported from our laboratories, may also provide greater potency Barchechath, S. D., et al., *Bioorg Med Chem Lett.* 2005, 15, 1785-1788.

Thus, we report the synthesis and structure activity relationship of novel derivatives and analogs of PFT-α, and corresponding closed ring counterparts, with enhanced potency and stability. To determine activity, we used a p53-independent assay of cell death wherein mouse thymocytes were treated with dexamethasone in the presence or absence of test compounds. In addition, we confirmed the activity of the most potent compounds in a p53-dependent apoptosis assay.

In addition, there is a need for novel, potent, and selective agents to prevent detrimental effects upon cells due to DNA damage, such as caused by chemotherapy, radiation, ischemic event, including ischemia-reperfusion injury and organ transplantation, and the like. There is also a need for pharmacological tools for the further study of the physiological processes associated with intracellular DNA damage.

A continuing need exists for compounds that can protect mammalian cells from the damaging effects of chemotherapy and irradiation, or in other situations in which it is desirable to protect tissue from the consequences of clinical or environmental stress.

SUMMARY OF THE INVENTION

The present invention provides compounds that can protect mammalian cells from the damaging effects of chemotherapy and irradiation, or in other situations in which it is desirable to protect tissue from the consequences of clinical or environmental stress. Accordingly, there is provided compounds of formula (I) and a method of protecting the cells comprising administering to a mammal in need of said suppression an effective amount of a compound of formula (I):

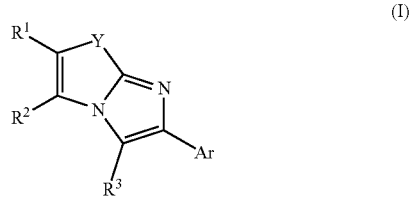

wherein $R^1$, $R^2$ and $R^3$ are independently hydrogen, halo, hydroxy, cyano, $N(R_a)(R_b)$, $S(R_a)$, $NO_2$, $(C_1-C_6)$alkyl, $(C_1-C_6)$alkoxy, $(C_2-C_6)$alkynyl, $(C_2-C_6)$alkenyl, $(C_2-C_7)$alkanoyl, $(C_2-C_7)$alkanoyloxy, or $(C_3-C_7)$cycloalkyl or $R^1$ and $R^2$ taken together are benzo, optionally substituted by $R^1$, or are $(C_3-C_5)$alkylene or methylenedioxy; wherein $R_a$ and $R_b$ are each independently hydrogen, $(C_1-C_3)$alkyl, $(C_2-C_4)$alkanoyl, phenyl, benzyl, or phenethyl; or $R_a$ and $R_b$ together with the nitrogen to which they are attached are a 5-6 membered heterocyclic ring, preferably a pyrrolidino, piperidino or morpholino ring;

Ar is aryl, heteroaryl, or a 5-6 membered heterocyclic ring, preferably comprising 1-3 $N(R_a)$, non-peroxide O or S atoms, such as a pyrrolidino, piperidino or morpholino ring, optionally substituted with 1-5, preferably 1-2, halo, $CF_3$, hydroxy, CN, $N(R_a)(R_b)$, $(C_1-C_6)$alkyl, $(C_1-C_6)$alkoxy, $(C_2-C_7)$alkanoyl, $(C_2-C_7)$alkanoyloxy, $(C_3-C_7)$cycloalkyl, $(C_2-C_6)$alkanoyl, $(C_2-C_6)$alkenyl, or phenyl;

Y is oxy (—O—), $S(O)_{0-2}$, Se, $C(R^1)(R^3)$, $N(R_a)$, or —P—;

or a pharmaceutically acceptable salt thereof.

Preferably, Ar is not substituted with halo or alkoxy. Preferably, Ar is heteroaryl or a heterocyclic ring. Preferably, $R^1$ and $R^2$ are not benzo or $(C_3-C_5)$alkylidenyl when Ar is aryl, e.g., is phenyl or napthyl. Novel compounds of formula (I) are also within the scope of the present invention, e.g., preferably Y is —O—, —Se—, $C(R_1)(R_3)$ or P. Preferably, Ar is heteroaryl. Preferably, Ar is substituted with CN, $(C_2-C_7)$alkanoyl), $(C_2-C_7)$alkanoyloxy, $(C_3-C_7)$cycloalkyl, $(C_2-C_6)$alkenyl or combinations thereof. Preferably, $R^1$, $R^2$ and $R^3$ are independently, OH, CN $(N(R_a)(R_b)$, $S(R_a)$, $NO_2$, $(C_2-C_7)$alkanoyl, or $(C_2-C_7)$alkanoyloxyl.

In a specific embodiment the compounds of the invention have formula (IA):

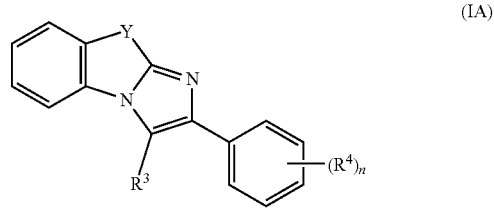

wherein $R^3$, hydrogen, halo, hydroxy, cyano, $-N(R^a)(R^b)$, $-S(R^a)$, $-NO_2$, $(C_1-C_6)$alkyl, $(C_1-C_6)$alkoxy, $(C_2-C_6)$alkynyl, $(C_2-C_6)$alkenyl, $(C_2-C_7)$alkanoyl, $(C_2-C_7)$alkanoyloxy, or $(C_3-C_7)$cycloalkyl; each $R^4$ is independently halo, $-CF_3$, hydroxy, $-CN$, $-N(R^a)(R^b)$, $(C_1-C_6)$alkyl, $(C_1-C_6)$alkoxy, $(C_2-C_7)$alkanoyl, formyl, $(C_2-C_7)$alkanoyloxy, $(C_3-C_7)$cycloalkyl, $(C_2-C_6)$alkanoyl, $(C_2-C_6)$alkenyl, or phenyl; wherein $R^a$ and $R^b$ are each independently hydrogen, $(C_1-C_3)$ alkyl, $(C_2-C_4)$alkanoyl, phenyl, benzyl, or phenethyl; or $R^a$ and $R^b$ together with the nitrogen to which they are attached are a 5-6 membered heterocyclic ring, preferably a pyrrolidino, piperidino or morpholino ring; Y is oxy (—O—), $-S(O)_{0-2}$—, or $-N(R^a)$—; n is 1, 2, 3, 4, or 5; or a pharmaceutically acceptable salt thereof.

Additionally, the invention provides a therapeutic method for preventing or reducing the damaging effects of chemotherapy and irradiation, or in other situations in which it is desirable to protect tissue from the consequences of clinical or environmental stress comprising administering to a mammal in need of such therapy, an effective amount of one or more compounds of formula (I), or a pharmaceutically acceptable salt thereof. Such pathological conditions or symptoms include blocking, moderating or reversing the deleterious effects of chemotherapeutic agents, particularly those which damage DNA; radiation, particularly radiation therapy (gamma-, beta- or UV-radiation), ischemic event, including stroke, infarct, ischemia-reperfusion injury and ischemia due to organ, tissue or cell transplantation; environmental pollution or contamination and the like.

The invention provides pharmaceutical compositions comprising novel compounds of formula (I), or a pharmaceutically acceptable salt thereof, in combination with a pharmaceutically acceptable diluent or carrier.

The invention provides a compound of formula (I) for use in medical therapy as well as the use of a compound of formula (I) for the manufacture of a medicament for the treatment of a pathological condition or symptom in a mammal, such as a human, induced cellular damage, i.e., with unwanted apoptosis.

The invention also includes a method for binding a compound of formula (I) to cells and biomolecules comprising p53 or p53 dependent receptors, in vivo or in vitro, comprising contacting said cells or biomolecules with an amount of a compound of formula (I) effective to bind to said receptors. Cells or biomolecules comprising ligand-bound p53 or p53 dependent receptor sites can be used to measure the selectivity of test compounds for specific receptor subtypes, or can be used as a tool to identify potential therapeutic agents for the treatment of diseases or conditions associated with p53 dependent activation, by contacting said agents with said ligand-receptor complexes, and measuring the extent of displacement of the ligand and/or binding of the agent, by methods known to the art.

BRIEF DESCRIPTION OF THE FIGURES

FIGS. 1A and 1B are open ring compounds exhibiting some cytoxicity, FIGS. 1C and 1D are closed ring compounds exhibiting no toxicity.

DETAILED DESCRIPTION

Figure 1A:
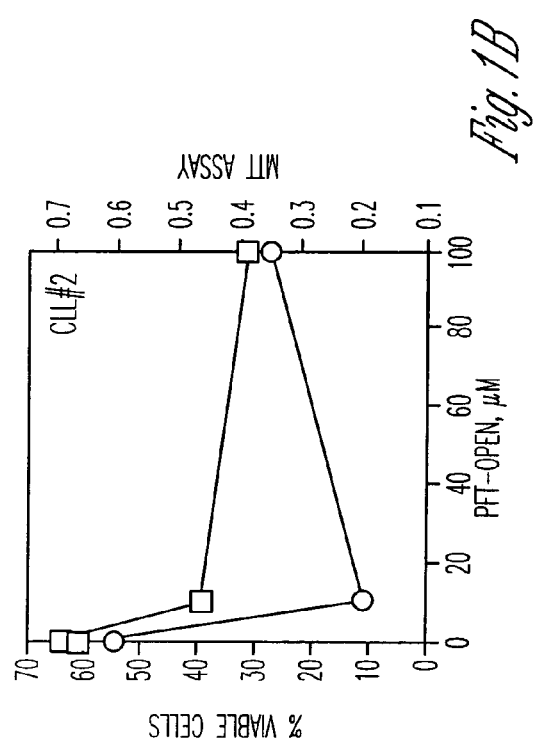
FIGS. 1A-1D depict the effects of IBT and PFT-α on B-CLL viability.
Figure 1C:
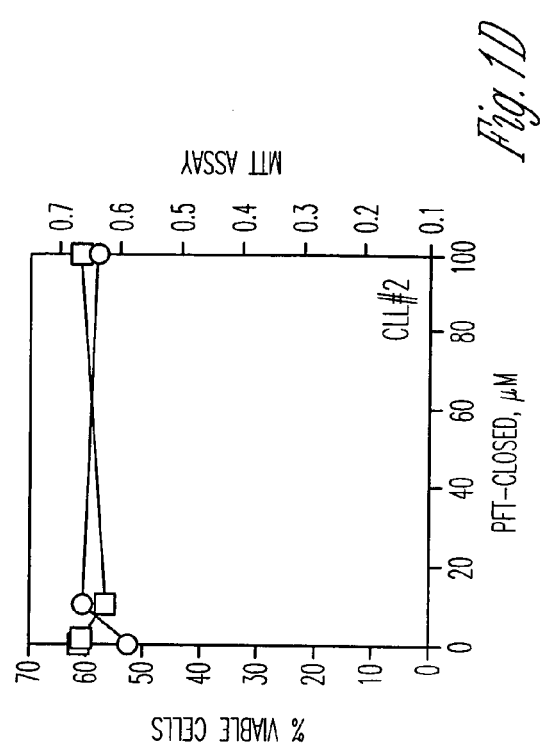
Figure 1B:
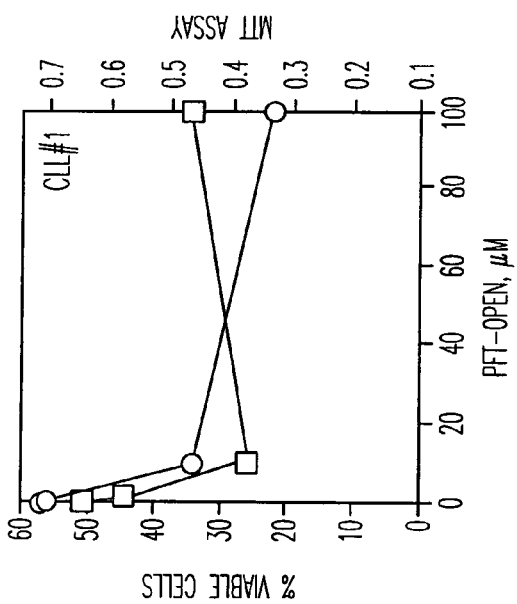
Figure 1D:
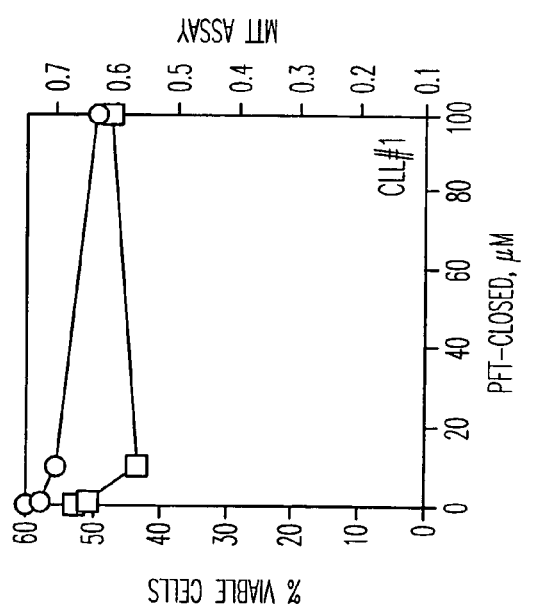
Figure 2A:
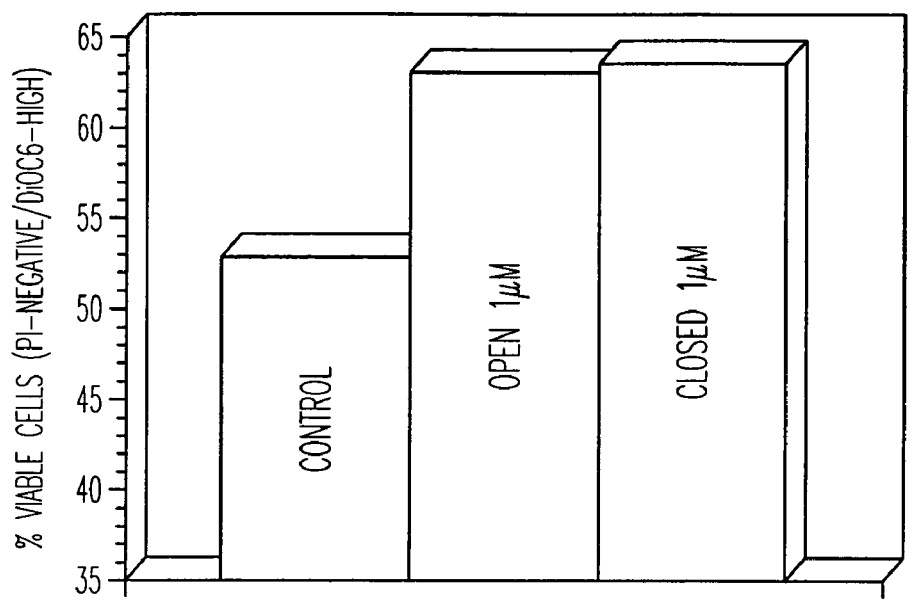
FIGS. 2A and 2B depict the protective effect of IBT against spontaneous apoptosis and against fludarabine-induced apoptosis.
Figure 2B:
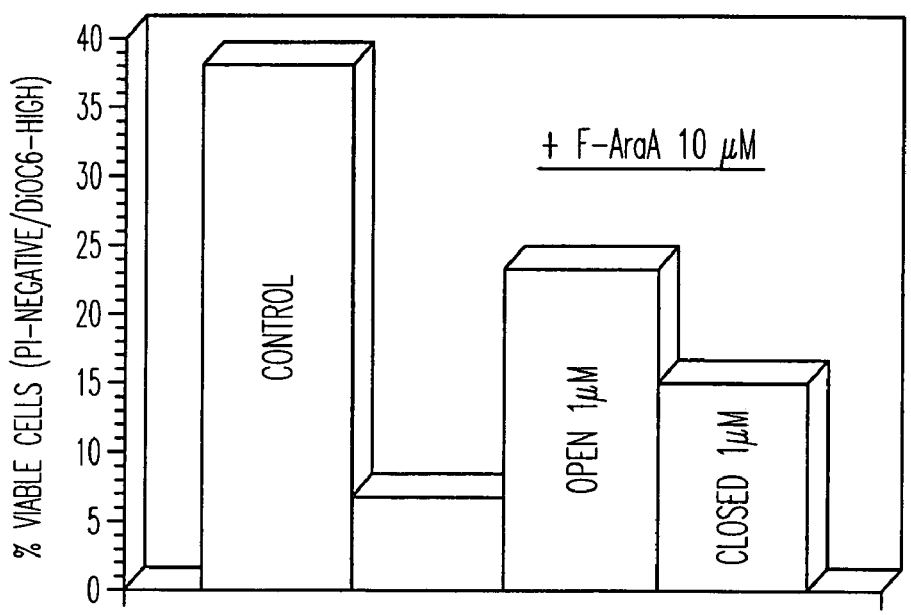
Figure 3A:
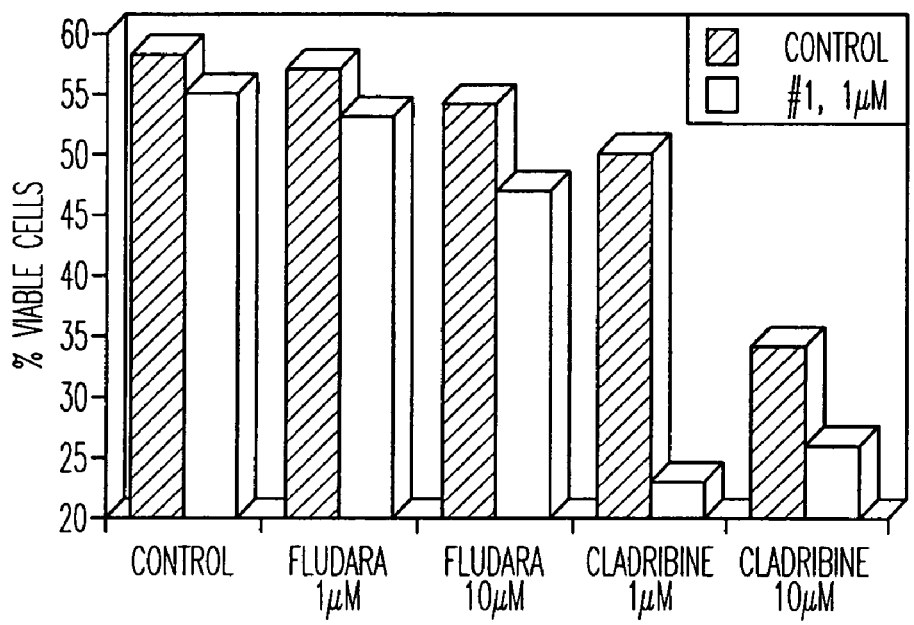
FIGS. 3A and 3B depict the ability of compounds of the invention to reduce the survival of malignant B cells from a patient with chronic lymphocytic leukemia maintained in tissue culture for 72 hours.
Figure 3B:
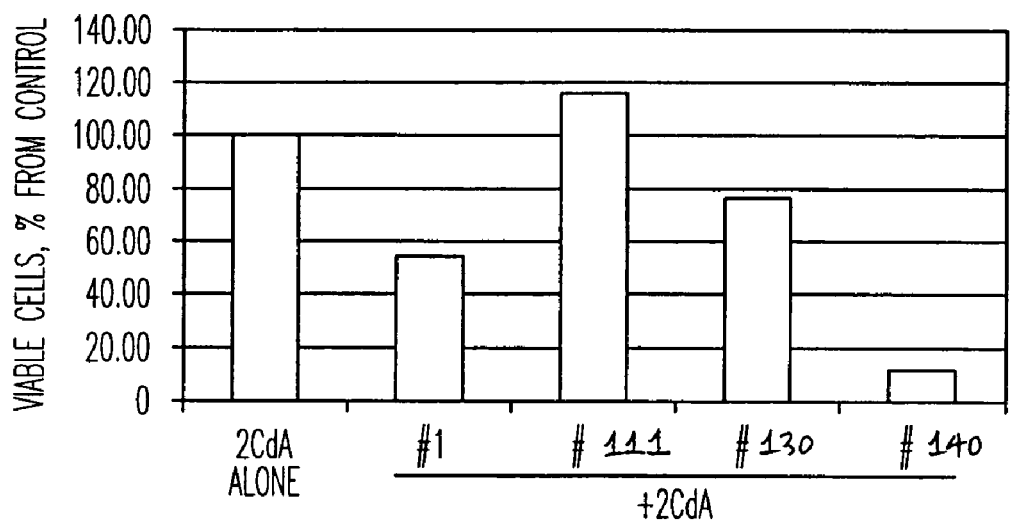
Figure 4A:
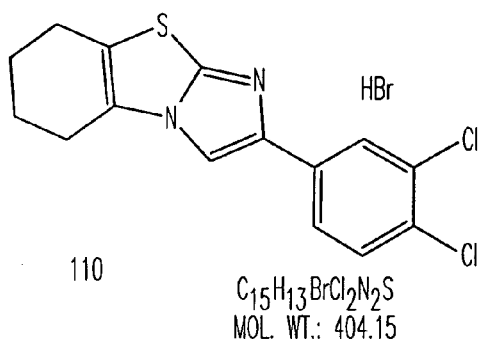
FIG. 4A-4O show the structures of compounds numbered in FIGS. 3-4. Compound 1 is PFT-α (control).
Figure 4B:
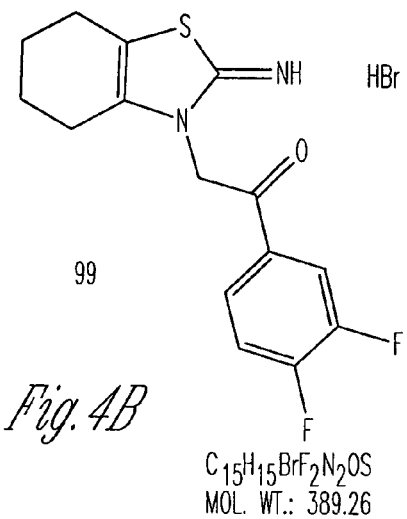
Figure 4C:
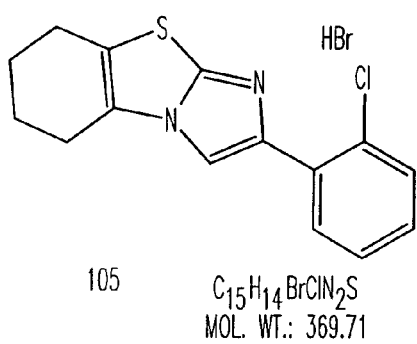
Figure 4D:
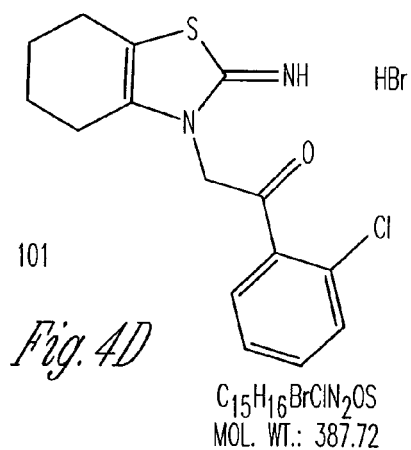
Figure 4E:
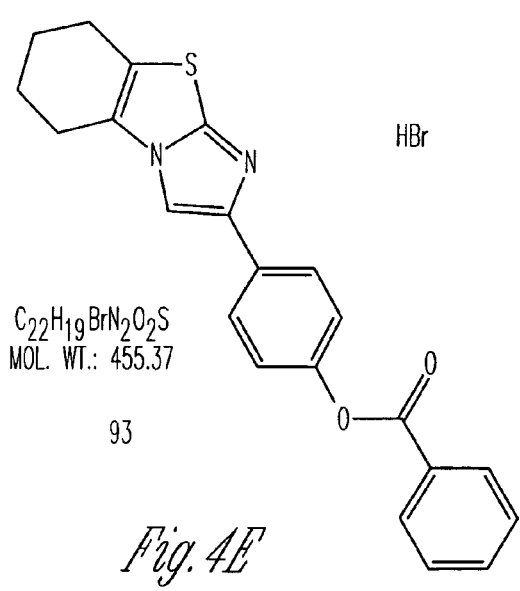
Figure 4F:
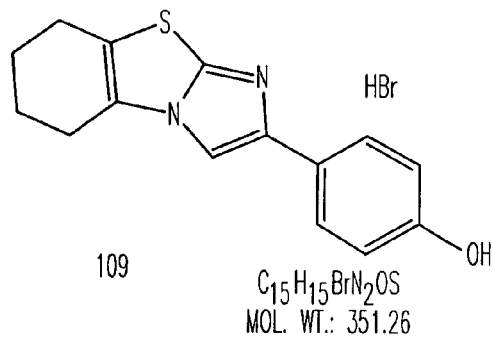
Figure 4G:
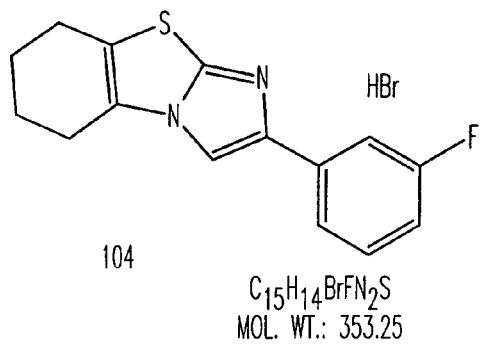
Figure 4H:
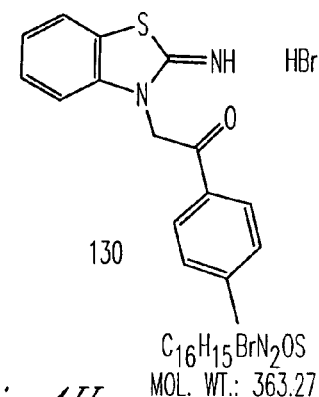
Figure 4I:
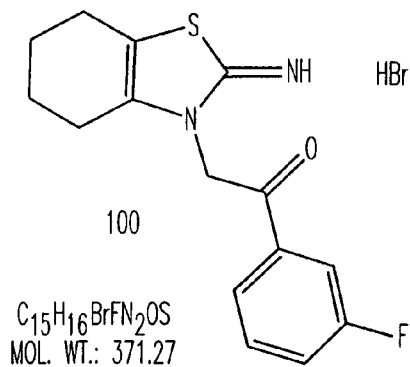
Figure 4J:
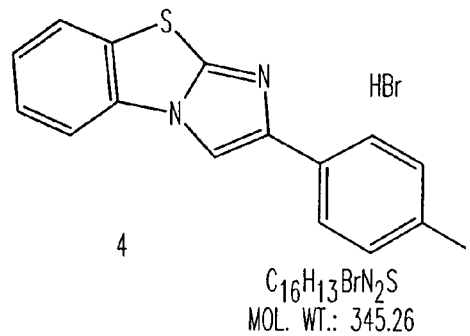
Figure 4K:
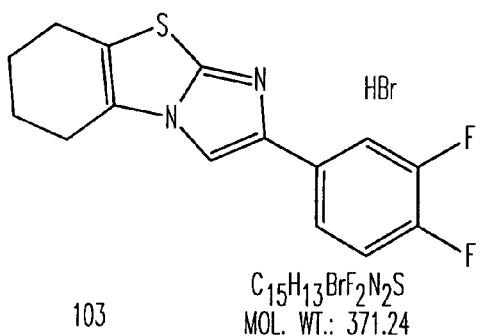
Figure 4L:
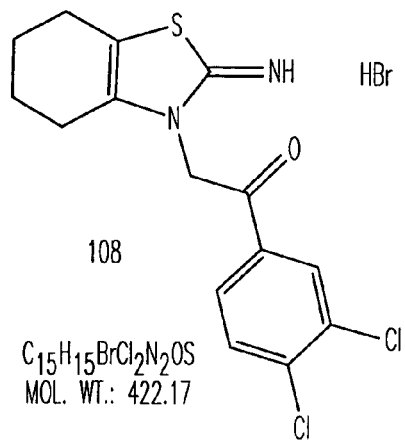
Figure 4M:
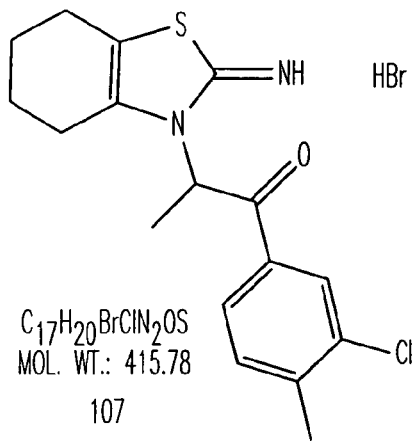
Figure 4N:
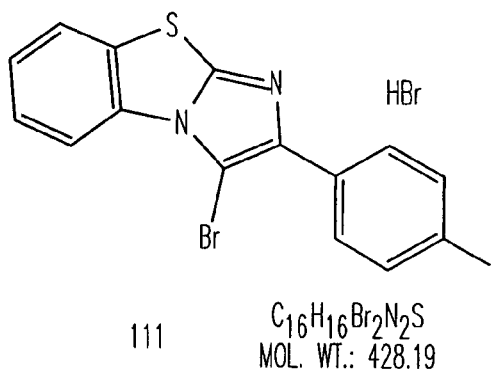
Figure 4O:
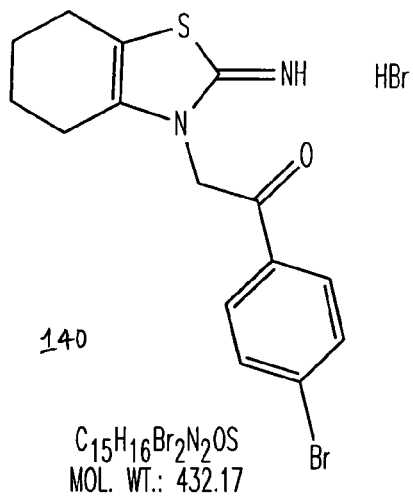

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring nitrogen or carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl. Heteroaryl also includes a radical of an ortho-fused bicyclic heterocycle of about eight to ten ring atoms, particularly a benzo-derivative or one derived by fusing a propylene, trimethylene, or tetramethylene diradical thereto. Preferred heteroaryls include pyridin-4-yl and thiophen-2-yl. The term "heterocyclic ring" "heterocycle," or "heterocycyl," is defined as above for formula (I).

It will be appreciated by those skilled in the art that compounds of the invention having a chiral center may exist in and be isolated in optically active and racemic forms. Some compounds may also exhibit polymorphism. It is to be understood that the present invention encompasses any racemic, optically active, polymorphic, or steroisomeric form, or mixtures thereof, of a compound of the invention, which possess the useful properties described herein, it being well known in the art how to prepare optically active forms (for example, by resolution of the racemic form by recrystallization techniques, by synthesis from optically active starting materials, by chiral synthesis, or by chromatographic separation using a chiral stationary phase) and how to determine cell protection activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_7$)cycloalkyl can be cyclopropyl, cyclobutyl, cyclopentyl, or cyclohexyl; the term cycloalkyl includes (cycloalkyl)alkyl of the designated number of carbon atoms; ($C_3$-$C_5$)cycloalkyl($C_2$-$C_4$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylmethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_2$-$C_7$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^3$ is H.

A specific value for Y is —S—, —O—, or —N($R^a$)—.

A more specific value for Y is —S—.

A specific value for $R^4$ is hydroxy, —N($R^a$)($R^b$), ($C_1$-$C_6$)alkyl, ($C_1$-$C_6$)alkoxy, or ($C_2$-$C_7$)alkanoyl.

Another specific value for $R^4$ is hydroxy, —N($R^a$)($R^b$), or ($C_1$-$C_6$)alkyl.

A more specific value for $R^4$ is —N($R^a$)($R^b$), or ($C_1$-$C_4$) alkyl.

Another specific value for $R^4$ is methyl, ethyl or propyl.

A more specific value for $R^4$ is methyl.

Another specific value for $R^4$ is —N($R^a$)($R^b$).

Another specific value for $R^4$ is —N($CH_2CH_3$)$_2$.

A specific value for —N($R^a$)($R^b$) is a 5-6 membered heterocyclic ring, optionally comprising 1, 2, or 3 N($R^a$), non-peroxide O or S atoms.

Another specific value for —N($R^a$)($R^b$) is pyrrolidino, piperidino or morpholino.

A more specific value for —N($R^a$)($R^b$) is pyrrolidino.

A specific compound of the invention is formula (IB):

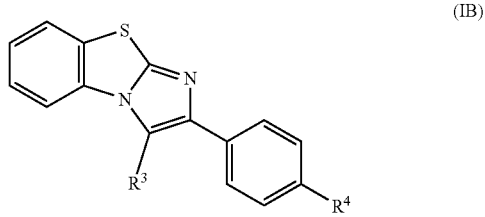

(IB)

where for $R^3$ is H.

The compounds of the invention, can be synthesized as illustrated in Scheme 1, starting with commercially available 2-aminobenzothiazoles. Alkylation of the 2-aminobenzothiazoles with various α-haloacetophenones provides the corresponding N-alkylated compounds, with alkylation occurring exclusively at the ring nitrogen. In protic solvents the ring alkylated fused thiazoles often formed aromatic ring-closed products with concomitant dehydration, leading to the corresponding closed ring derivatives. The corresponding IBT derivatives such as, for example, 3-15 can then be prepared by ring closure in refluxing ethanol or in methoxyethanol when higher temperatures were needed. Additional methods for preparing the compounds of the invention are described in Barchechath, S. et al., *J Med Chem.* 2005, 48, 6409-6422.

Scheme 1

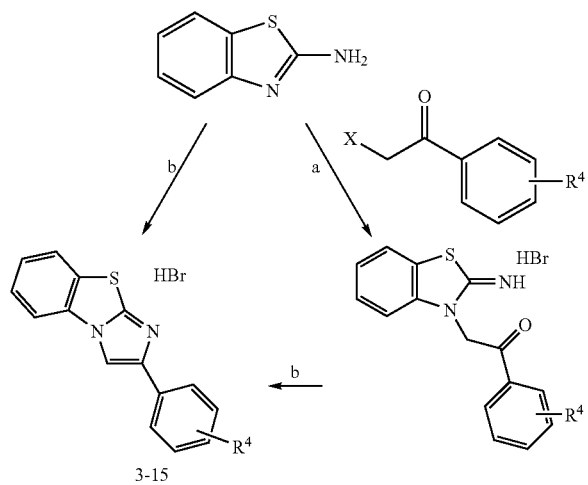

(a.) toluene, room temperature, 24-48 hours; (b.) ethanol or methoxyethanol, reflux, 1.5 hours.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula (I) can be formulated as pharmaceutical compositions and administered to a mammalian host, such as a human cancer patient, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glycerol esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelation.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1-25 wt %, preferably from about 0.5-10 wt %. The concentration in a semi-solid or solid composition such as a gel or a powder will be about 0.1-5 wt %, preferably about 0.5-2.5 wt %.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form, for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

The ability of a compound of the invention to act as a suppressor of p53 activity may be determined using pharmacological models which are well known to the art, e.g., as disclosed below.

The invention will now be illustrated by the following non-limiting Examples.

Biology. To examine the relative protective effect of the compounds a reliable and relatively rapid screening assay was required. We and others have found that the structural similarity of PFT-α and IBT with luciferin rendered luciferase-based reporter gene assays for apoptosis unreliable.[19] Instead we assayed fluorescent dye retention described below in thymocytes after dexamethasone induced apoptosis. Dexamethasone (DEX) treatment of lymphocytes from the thymus initiates a signaling pathway that converges on the mitochondria-mediated molecular executioner cascade, leading to apoptosis within six hours.[20] The six hour time point was chosen, as PFT-α was reported to inhibit DEX-induced apoptosis within this incubation period, and in our hands was found to be reliable and reproducible.[5]

Figure 7:
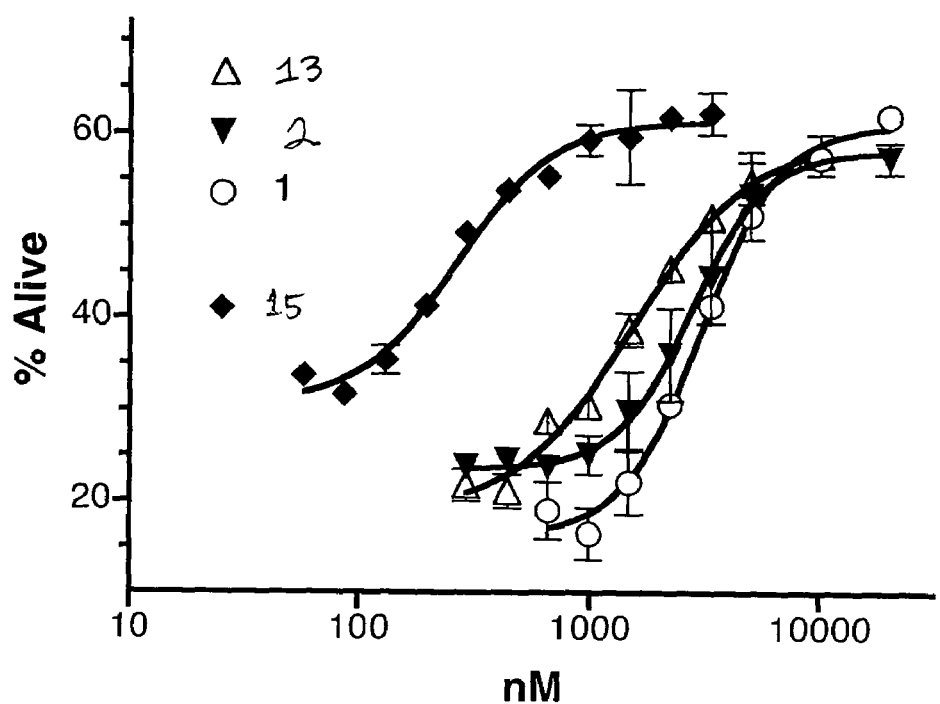
FIG. 7. shows the inhibition of dexamethasone induced thymocyte cell death. Murine thymocytes were pretreated with graded quantities of the indicated compounds. Apoptosis was then induced with 5 μM dexamethasone. After 6 hours the cells were stained with $DiOC_6$ and PI and assayed for survival by flow cytometry. Shown are the percentages of living cells at the end of 6 hours for three independent experiments.
Figure 8:
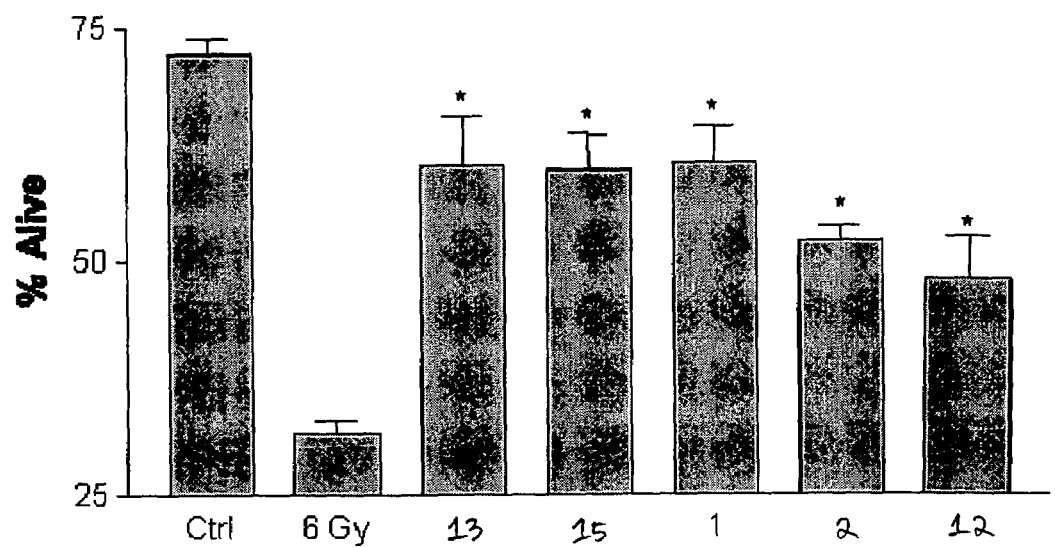
FIG. 8. shows the inhibition of gamma radiation-induced apoptosis. Ten million thymocytes per well were pretreated with 5 μM of the indicated compounds for 30 minutes and then irradiated with 6 Gy. After 6 hours the cells were stained with $DiOC_6$ and PI and assayed for survival by flow cytometry. Shown are the average percent survival pooled from two experiments with the SEM. Compounds that significantly improved viability after irradiation are indicated by an asterisk ($P<0.01$ by Students t test).

All of the compounds were screened in the thymocyte assay for cytotoxicity and their ability to prevent dexametha sone-induced cell death. Murine thymocytes were exposed to 10 μM or 5 μM of each compound in the presence or absence of DEX for six hours and then assayed for their in vitro viability by 3,3'-dihexyloxacarbocyanine iodide ($DiOC_6$) and propidium iodide (PI) staining, and flow cytometry. When cell death signals converge on the mitochondria, there is a loss of the inner mitochondrial membrane potential and cells can no longer retain the dye $DiOC_6$ as an indicator of apoptosis. Once cells lose the integrity of the outer cell membrane, then the dye propidium iodide is no longer excluded from these cells. The percentage of viable cells, which retained $DiOC_6$ and excluded PI was compared to cells treated with DEX alone. Compounds that significantly enhanced survival in repeated determinations (P≦0.01) were then selected for dose response study to determine the $EC_{50}$ (Tables 1, 2, and FIG. 7).

TABLE 2

$EC_{50}$ (μM) of compounds in thymocyte apoptosis assay

| $R_1$ substituent | Compound # | $EDEC_{50}$ (μM) | 95% confidence interval (μM) |
|---|---|---|---|
| methyl | 13 | 1.22 > 10 | 0.95-1.57 |
| phenyl | 10 | 8.12 7.26 | 4.08-13.75 6.02-8.76 |
| 2-naphthyl | 14 | 4.02 > 10 | 3.45-4.69 |
| pyrrolidinyl | 15 | 0.35 9.84 | 0.11-1.08 2.78-34.83 |

The effects of substitution at the para position of the phenyl ring of 1 and corresponding derivatives were investigated. A variety of substituents was selected on the basis of their electronic and lipophilic properties. These ability of these compounds to prevent cell death are shown in Table 3.

TABLE 3

Survival of cells treated with IBT and analogues when challenged with DEX

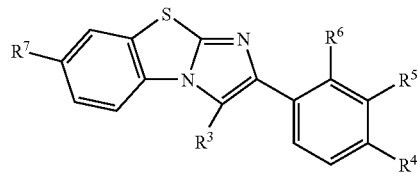

| Compound # | $R^4$ | $R^5$ | $R^6$ | $R^3$ | $R^7$ | Average cell survival (%)[a] Average alive cells (%)[a] | Standard deviation | Mann-Whitney U test |
|---|---|---|---|---|---|---|---|---|
| 3 | furanyl | H | H | H | H | 16 | 13 | 0.0553 |
| 4 | Me | H | H | H | OH | 19[b] | 10 | 0.0009 |
| 5 | Br | H | H | H | H | 22 | 10 | 0.0829 |
| 6 | Me | H | H | Br | H | 24[b] | 10 | 0.0829 |
| 7 | Me | H | H | H | $NH_2$ | 27 | 22 | 0.4114 |
| 8 | cyclopentyl | H | H | H | H | 36 | 2 | 0.9517 |
| 9 | Me | H | H | H | Br | 39 | 3 | 0.8286 |
| 10 | Ph | H | H | H | H | 59 | 2 | 0.0009 |
| 11 | Me | H | H | H | OMe | 68[b] | 14 | 0.0009 |
| 12 | H | H | H | H | H | 73 | 1 | 0.0019 |
| 13 | Me | H | H | H | H | 73[b] | 5 | 0.0003 |
| 14 | 2-naphthyl | H | H | H | H | 75[b] | 2 | 0.0009 |
| 15 | pyrrolidinyl | H | H | H | H | 78[b] | 1 | 0.0003 |

[a]Control average % cell survival 72 ± 4, Dexamethasone average % cell survival 36 ± 7
[b]Toxic at 10 μM, tested at 5 μM

TABLE 1

$EC_{50}$ (μM) of compounds in thymocyte apoptosis assay

| Compound # | $EDEC_{50}$ (μM) | 95% Confidence Interval (μM) |
|---|---|---|
| 11 | 4.44 | 2.86.6.89 |
| 12 | 10.23 | 8.49-12.32 |

Chemistry. Melting points were obtained on a Mel-temp II capillary melting point apparatus and are uncorrected. Proton nuclear magnetic resonance spectra were obtained on a Varian Unity 500 at 499.8 MHz, or on a Varian Mercury at 400.06 MHz. The chemical shifts are expressed in δ values (parts per million) relative to tetramethylsilane (TMS) as internal standard. High resolution mass spectrometric analysis were performed on a Finnigan MAT900XP high resolution double focusing mass spectrometer using electron impact. Elemental analyses were performed by NuMega Resonance Labs, San Diego, Calif. Thin-layer chromatography was performed on silica gel 60 F-254 plates (EM Reagents). E Merck silica gel (230-400 mesh) was used for flash column chromatography.

Biological Materials.

Mice. C57B1/6 and p53$^{-/-}$ mice were purchased from The Jackson Laboratories (Bar Harbor, Me.). The mice were bred and maintained under standard conditions in the University of California, San Diego Animal Facility that is accredited by the American Association for Accreditation of Laboratory Animal Care. All animal protocols receive prior approval by the institutional review board.

Reagents. Dexamethasone (DEX) was purchased from Sigma-Aldrich (St. Louis, Mo.). Other chemicals were purchased from Maybridge plc (Trevillett, Tintagel, Cornwall, UK), and Lancaster Synthesis (Windham, N.H.).

Apoptosis assays. Thymocytes were harvested from young C57B1/6 mice and cultured at 37° C. in 5% $CO_2$ in RPMI 1640 containing 10% FBS, 1% Penicillin/Streptomycin (Gibco BRL, Rockville, Md.). Thymocytes were plated at a density of $10^7$ cells/mL and pre-incubated with 5-10 µM of each compound (from 10 mM stock in DMSO) for 30 minutes before induction of apoptosis. Apoptosis was induced with 5 µM dexamethasone or by exposure to 6 Gy gamma radiation. After 6 hours, cell apoptosis was assayed by propidium iodide (PI) and 3,3' dihexyloxacarbocyanine iodide ($DiOC_6$) staining. The cells were removed from the plate and incubated for 30 minutes in medium with 40 nM $DiOC_6$ and 5 µg/mL PI and then analyzed by flow cytometry in a FACS caliber (Beckton-Dickinson, San Jose, Calif.). Viable cells had high $DiOC_6$ (FL-1) and low PI (FL-3), whereas apoptotic cells had low $DiOC_6$ (FL-1) and low PI (FL-3). To evaluate the $EC_{50}$s the thymocytes were pre-exposed to graded concentrations of selected compounds for 30 minutes and then apoptosis was induced with 5 µM dexamethasone. After 6 hours the cells were harvested and stained as above.

$EC_{50}$ Determination

The concentration ($EC_{50}$) of each compound that inhibited dexamethasone-induced cell death by 50% was determined by nonlinear regression fitting of the data to a one-site model. Pseudo Hill slopes were determined by nonlinear regression fit of the data to a sigmoidal dose-response equation (variable slope): % viability=minimum % viability+(maximum−minimum % viability)/[1+10(log $EC_{50}$−X)$^n$], where X is the logarithm of inhibitor concentration, and n is the pseudo Hill slope and the maximum and minimum % viability were experimentally determined after dexamethasone exposure and drug treatment. $EC_{50}$ values and 95% confidence intervals (CI) were derived from the sigmoid fits to the percent control transformed data shown using GraphPad Prism version 4.0b for Macintosh (GraphPad Software, San Diego, Calif.).

Immunoblotting

After removal of medium, cells were disrupted in lysis buffer (10 mM HEPES pH 7.9, 10 mM KCl, 0.1 mM EDTA, 0.1 mM EGTA, 1 mM dithiothreitol, 0.5 mM phenylmethylsulfonyl fluoride, and 0.6% NP-40) on ice. The nuclei were separated by centrifugation and the cytoplasmic sample removed. The nuclear pellets were resuspended in (20 mM HEPES pH 7.9, 0.4 M NaCl, 1.0 mM EDTA, 1.0 mM EGTA, 1 mM dithiothreitol, 0.1 mM phenylmethylsulfonyl fluoride) and the insoluble material was removed by centrifugation. The samples were heated to 70° C. for 10 minutes in loading buffer with 10 mM DTT. Each lane of an SDS-PAGE gel was loaded with 20 µg of protein. After electrophoresis, the proteins were transferred to a polyvinylidene difluoride (PVDF) membrane, blocked with 2% I-block™ (Tropix Inc, Bedford, Mass.) containing 0.05% Tween-20 in PBS, and then incubated with anti-PUMA (AbCam, Inc., Cambridge, Mass.). Horseradish peroxidase-conjugated anti-IgG (Santa Cruz Laboratories, Santa Cruz, Calif.) was used as the secondary antibody. The membranes were developed using a chemiluminescence system (ECL detection reagent: Amersham Life Science, Aylesbury, UK). The membranes were reprobed with anti-actin (Sigma, St Louis, Mo.) to ensure equivalent loading.

Synthesis

Method A : General procedure for synthesis of PFT-α derivatives and aromatic analogs. Following a procedure reported by Singh et al., *Indian J. Chem., Sect. B* 1976, 14B, 997-998, a mixture of 2-amino-4,5,6,7-tetrahydrobenzothiazole (1 eq.) and the appropriate phenacyl bromide (1.1 eq.) was stirred in toluene at room temperature for 24 to 48 hours. The product crystallized out and was collected by filtration. The same procedure was used to synthesize aromatic analogs starting from commercially available of 2-aminobenzothiazole, some bearing a substituent on C-6. The aromatic analogs were made using the same procedures.

General Procedure for Synthesis of Aromatic Analogs of IBT Derivatives.

Method B: one-step ring closure. A mixture of 2-aminobenzothiazole (1 eq.) and the appropriate phenacyl bromide (1.1 eq.) was refluxed in ethanol for 90 minutes. The ring-closed product crystallized out upon cooling and was separated by filtration.

Method C: two-step ring closure. 2-imino-3-phenacyl-benzothiaole hydrobromide or analog was refluxed in ethanol for 90 minutes. The ring-closed product crystallized out upon cooling and was separated by filtration.

EXAMPLE 1

1-(4-cyclopentylphenyl)-2-(2-iminobenzothiazol-3 (2H)-yl)ethanone hydrobromide salt (16)

The title compound is prepared from α-bromo-4-(1-cyclopentyl)aceto-phenone (Hai et al., *J. Org. Chem.,* 1958, 23, 39-42; Vejdelek et al., *Collect. Czech. Chem. Commun.* 1983, 48, 642-648) and 2-aminobenzothiazole using method A in 16% yield: mp 186-190° C. (dec.); $^1$H-NMR (DMSO-d$_6$) 1.59 (m, 2H), 1.69, (m, 2H), 1.81 (m, 2H), 2.07 (m, 2H), 3.12 (m, 1H), 6.07 (s, 2H), 7.44 (d, 2H), 7.52 (m, 2H), 7.69 (t, 1H), 7.84 (t, 1H), 8.03 (d, 2H), 9.13 (s, 1H); HR-MS (FAB) m/z 337.1376 (M$^+$); Anal. calculated for $C_{20}H_{21}BrN_2OS$: C, 57.56; H, 5.07; N, 6.71, found; C, 50.82; H, 4.21; N, 7.65.

EXAMPLE 2

2-(2-Imino-benzothiazol-3-yl)-1-(4-pyrrolidin-1-yl-phenyl)-ethanone hydrobromide salt (17)

The title compound is prepared from α-bromo-4-(1-pyrrolidino)acetophenone and 2-amino-4,5,6,7-tetrahydrobenzothiazole using method A in 43% yield: mp 285-290° C. (dec); $^1$H-NMR (DMSO-d$_6$) 2.00 (s, 4H), 3.38 (m, 4H), 5.93 (s, 2H), 6.68 (d, 2H), 7.43 (t, 1H), 7.50 (t, 1H), 7.57 (d, 1H), 7.90 (d, 2H), 8.03 (d, 1H); Anal. $C_{19}H_{20}BrN_3OS$ (C, H, N).

EXAMPLE 3

2-Furan-2-yl-imidazo[2,1-b]benzothiazole hydrobromide salt (3)

The title compound is prepared from 2-Bromo-1-furan-2-yl-ethanone and 2-aminobenzothiazole using method B in 30% yield: mp>250° C. (dec); $^1$H-NMR (DMSO-$d_6$) 6.63 (s, 1H), 6.78 (s, 1H), 7.48 (t, 1H), 7.60 (t, 1H), 7.77 (s, 1H), 8.09 (d, 1H), 8.13 (d, 1H), 8.68 (s, 1H); Anal. ($C_{13}H_9BrN_2OS$ ⅔ $H_2O$) C, H, N.

EXAMPLE 4

2-p-Tolyl-benzo[d]imidazo[2,1-b]thiazol-7-ol (4)

A mixture of 9 (362 mg, 0.845 mmol) and copper (I) oxide (46 mg, 0.321 mmol) in a 30% aq. solution of NaOH (4 mL) was heated in a bomb for 4 hours. The mixture was neutralized and extracted with EtOAc. The solid recovered upon evaporation was purified by preparative TLC to give 4 in 47% yield: mp 275-277° C.; $^1$H-NMR (DMSO-$d_6$) 2.31 (s, 3H), 6.95 (dd, 1H), 7.22 (d, 2H), 7.38 (d, 1H), 7.72 (d, 2H), 7.77 (d, 1H), 8.60 (s, 1H), 9.95 (s, 1H); HR-MS (EI) m/z 280.0662 (M$^+$); Anal. calculated for $C_{16}H_{13}BrN_2OS$ ½ HBr: C, 59.90; H, 3.93; N, 8.73, found; C, 59.47; H, 4.43; N, 8.55.

EXAMPLE 5

3-Bromo-2-p-tolyl-imidazo[2,1-b]benzothiazole (6)

To a suspension of 13 (1.643 g, 4.76 mmol) in DMF (150 mL) at room temperature, was slowly added drop wise a solution of N-bromosuccinimide (933 mg, 5.24 mmol) in DMF (6 mL). The solvent was removed under high vacuum and the residue was slurried in ice water/ethanol (100 mL, 50%). A solid dropped out and was collected by filtration and rinsed with water to give 6 in 82% yield: mp>180° C. (dec); $^1$H-NMR (DMSO-$d_6$) 2.36 (s, 3H), 7.31 (d, 2H), 7.51 (t, 1H), 7.61 (t, 1H), 7.90 (d, 2H), 8.11 (d, 1H), 8.44 (d, 1H); Anal. ($C_{16}H$ IBrN$_2$S.⅓ $H_2O$ C, H, N.

EXAMPLE 6

2-p-Tolyl-imidazo[2,1-b]benzothiazol-7-ylamine (7)

To a suspension of 7-Nitro-2-p-tolyl-imidazo[2,1-b]benzothiazole hydrobromide salt (128 mg, 0.328 mmol) in water at 80° C. were added 4 portions (10 eq.) of sodium dithionite over 30 minutes whereupon the suspension become clear and decolorized to give 7 in 22% yield: mp>210° C. (dec.); $^1$H-NMR (DMSO-$d_6$) 2.32 (s, 3H), 6.80 (dd, 1H), 7.13 (d, 1H), 7.23 (d, 2H), 7.65 (d, 1H), 7.72 (d, 2H), 8.53 (s, 1H); HR-MS (EI) m/z 279.0821 (M$^+$); Anal. calculated for $C_{16}H_{13}N_3S$.⅔ HBr: C, 41.05; H, 3.30; N, 8.98; found; C, 41.81; H, 2.86; N, 6.10.

EXAMPLE 7

2-(4-Cyclopentyl-phenyl)-imidzxo[2,1-b]benzothiazoles hydrobromide salt (8)

The title compound is prepared from 16 using method C in 65% yield: mp 0.250° C. (dec.); $^1$H-NMR (DMSO-$d_6$) 1.57 (m, 2H), 1.66, (m, 2H), 1.79 (m, 2H), 2.03 (m, 2H), 3.00 (q, 1H), 7.33 (d, 2H), 7.45 (t, 1H), 7.59 (t, 1H), 7.78 (d, 2H), 8.01 (d, 1H), 8.06 (d, 1H), 8.77 (s, 1H); HR-MS (FAB) m/z 319.1267 (M$^+$); Anal. calculated for $C_{20}H_{18}N_2S$.¼ HBr: C, 70.93; H, 5.43; N, 8.27; found; C, 70.01; H, 5.82; N, 10.97.

EXAMPLE 8

7-Bromo-2-p-tolylimidazo[2,1-b]benzothiazole hydrobromide salt (9)

The title compound is prepared from 2-bromo-4'-methylacetophenone and 2-amino-6-bromobenzothiazole using method B in 24% yield: mp 205-208° C.; $^1$H-NMR (DMSO-$d_6$) 2.31 (s, 3H), 7.23 (d, 2H), 7.73 (m, 3H), 7.91 (d, 1H), 8.32 (s, 1H), 8.70 (s, 1H); HR-MS (EI) m/z 341.9822 (M$^+$).

EXAMPLE 9

7-Methoxy-2-p-tolyl-imidazo[2,1-b]benzothiazole hydrobromide salt (11)

The title compound is prepared from 2-bromo-4'-methylacetophenone and 2-amino-6-bromobenzothiazole using method B in 62% yield: mp 274-276° C. (dec.); $^1$H-NMR (DMSO-$d_6$) 2.33 (s, 3H), 3.84 (s, 3H), 7.18 (dd, 1H), 7.26 (d, 2H), 7.72 (m, 3H), 7.92 (d, 1H), 8.71 (s, 1H); Anal. ($C_{17}H_{15}BrN_2OS$) C, H, N.

EXAMPLE 10

2-(4-Pyrrolidin-1-yl-phenyl)-benzo[d]imidazo[2,1-b]thiazole hydrobromide salt (15)

The title compound is prepared from α-bromo-4-(1-pyrrolidino)acetophenone (Lancaster) and 2-aminobenzothiazole using method B and 10 hours of reflux in 16% yield: mp 283-287° C.; $^1$H-NMR (DMSO-$d_6$) 1.98 (m, 4H), 3.31 (m, 4H), 6.68 (m, 2H), 7.51 (d, 1H), 7.66 (d, 3H), 8.11 (m, 2H), 8.71 (s, 1H); Anal. ($C_{19}H_{18}BrN_3S$) C, H, N.

EXAMPLE 11

3-Benzyl-3H-benzothiazol-2-ylideneamine hydrochloride salt (18) (Zhu et al., *J. Med. Chem.* 2002, 45, 5090-5097)

A mixture of 2-aminobenzothiazole (2.116 g, 13.7 mmol), benzyl chloride (2.1 mL, 18.2 mmol) and sodium iodide (200 mg) were refluxed for 8 hours in methoxyethanol (25 mL). Crystallization occurred upon cooling. The crystals were filtered off and thoroughly washed with ether to give yellow crystals in 39% yield: mp 275-278° C.; $^1$H-NMR (DMSO-$d_6$) 5.65 (s, 2H), 7.28, (d, 2H), 7.36 (m, 4H), 7.50 (t, 1H), 7.55 (d, 1H) 8.02 (s, 1H); HR-MS (EI) m/z 240.0719 (M$^+$).

EXAMPLE 12

3-(4-Methyl-benzyl)-3H-benzothiazol-2-ylideneamine hydrochloride salt (19)

A mixture of 2-aminobenzothiazole (2.104 g, 13.6 mmol) and 4-methylbenzyl chloride (2.25 mL, 12.5 mmol) was refluxed for 8 hours in methoxyethanol in the presence of a catalytic amount of sodium iodide (220 mg, 1.46 mmol). After cooling a precipitate formed which was filtered and rinsed with ether to give 35% yield: mp 243-248° C.; $^1$H-NMR (DMSO-$d_6$) 2.26 (s, 3H), 5.65 (s, 2H), 7.20 (dd, 4H), 7.39 (t, 1H), 7.48 (t, 1H), 7.55 (d, 1H), 8.02 (d, 1H); HR-MS (EI) m/z 254.0870 (M$^+$).

EXAMPLE 13

N-(3H-Benzothiazol-2-ylidene)-4-methyl-benzenesulfonamide (20)

To a solution of 2-aminobenzothiazole (1.018 g, 6.78 mmol) in dry pyridine (4 mL) was added portion wise, p-toluene sulfonyl chloride (1.42 g, 7.48 mmol). The solution turned yellow upon addition. After 5 minutes of stirring at rt, the mixture was heated (70-80° C.) for 5 minutes. The mixture was poured on a bed of ice and the resulting precipitate was filtered off and dried overnight in a dessicator under vacuum to give a yellow powder in 93% yield: mp 246-249° C.; $^1$H-NMR (DMSO-d$_6$) 2.36 (s, 3H), 7.26, (dt, 1H), 7.30 (d, 1H), 7.37 (d, 2H), 7.40 (dt, 1H), 7.75 (d, 2H), 7.81 (d, 1H); Anal. ($C_{14}H_{12}N_2O_2S_2$) C, H, N.

EXAMPLE 14

4-Methyl-N-[3-(2-oxo-2-p-tolyl-ethyl)-3H-benzothiazol-2-ylidene]-benzenesulfonamide (21)

To a solution of 20 (930 mg, 3.01 mmol) in DMF (15 mL) at room temperature was added NaH. After the effervescence subsided, 2-bromo-4'-methylacetophenone (775 mg, 3.36 mmol) was added. The reaction was first stirred at room temperature for an hour and then heated at 80° C. until completion (by TLC). The mixture was allowed to cool before being poured on ice (400 mL). A precipitate dropped out. It was filtered and washed with cold water and dried to give a pale yellow powder in quantitative yield: mp 180-182° C.; $^1$H-NMR (DMSO-d$_6$) 2.35 (s, 3H), 2.43 (s, 3H), 5.86 (s, 2H), 7.33 (m, 3H), 7.42 (m, 3H), 7.57 (d, 1H), 7.64 (d, 2H), 7.91 (d, 1H), 7.97 (d, 2H); Anal. ($C_{23}H_{20}N_2O_3S_2$) C, H, N.

EXAMPLE 15

2-(Benzothiazol-2-ylsulfanyl)-1-p-tolyl-ethanone hydrobromide salt (22)

A mixture of 2-mercaptobenzothiazole (570 mg, 3.34 mmol) and 2-bromo-4'-methylacetophenone (870 mg, 3.67 mmol) was refluxed in ethanol (15 mL) for 90 minutes. The solution was cooled in the fridge to give a yellow solid in 18% yield: mp 76-78° C.; $^1$H-NMR (DMSO-d$_6$) 2.42 (s, 3H), 5.15 (s, 2H), 7.36 (t, 1H), 7.41 (d, 2H), 7.44 (t, 1H), 7.78 (d, 1H), 8.00 (m, 3H); Anal. ($C_{16}H_{14}BrNOS_2$·½ $H_2O$) C, H, N.

EXAMPLE 16

(2-Imino-4,5,6,7-tetrahydro-benzothiazol-3-yl)-acetic acid ethyl ester hydrobromide salt (23) (Zhu et al., *J. Med. Chem.* 2002, 45, 5090-5097)

A mixture of 2-amino-4,5,6,7-tetrahydrobenzothiazole (2.296 g, 14.9 mmol) and ethyl bromoacetate (2.747 g, 16.4 mmol) was refluxed in ethanol (50 mL) containing 3 drops of Et$_3$N for 90 minutes. The reaction mixture was concentrated to half volume in vacuo and the resulting precipitate was filtered and rinsed with cold ethanol, then ether to give a white powder in 79% yield: mp 222-224° C.; $^1$H-NMR (DMSO-d$_6$) 1.25 (t, 3H), 1.74 (d, 4H), 2.39 (s, 2H), 2.52 (m, 2H), 4.22 (q, 2H), 4.95 (s, 2H), 9.67 (s, 2H); Anal. $C_{11}H_{17}BrlN_2O_2S$ (C, H, N); HR-MS (EI) m/z 240.0931 (M$^+$).

EXAMPLE 17

4-Phenyl-1H-imidazole-2-thiol (24)

The title compound is synthesized following the procedure described by Maeda et al. (*Chem. Pharm. Bull.* 1984, 32, 2536-2543).

EXAMPLE 18

3-Phenyl-5,6,7,8-tetrahydroimidazo[2,1-b]benzothiazole hydrochloride salt (25)

A solution of 4-Phenyl-1H-imidazole-2-thiol 24 (Maeda et al., *Chem. Pharm. Bull.* 1984, 32, 2536-2543) and 2-chlorocyclohexanone was refluxed in butanol for 3 hours. After cooling, the resulting precipitate was filtered to give 25 in 75% yield: mp 274-278° C.; $^1$H-NMR (DMSO-d$_6$) 1.89 (m, 4H), 2.76 (m, 4H), 7.38 (t, 1H), 7.49 (t, 2H), 7.88 (d, 2H), 8.51 (s, 1H); HR-MS (EI) m/z 254.0874 (M$^+$).

EXAMPLE 19

2-(2-Imnino-thiazol-3-yl)-1-p-tolyl-ethanone hydrobromide salt (26)

The title compound is prepared from 2-bromo-4'-methylacetophenone and 2-aminothiazole using method A in 64% yield: mp>220° C. (dec); $^1$H-NMR (DMSO-d$_6$) 2.42 (s, 3H) 5.79, (s, 2H), 7.06 (d, 1H), 7.35 (d, 1H), 7.44 (d, 2H), 7.92 (d, 2H), 9.55, (s, 2H); Anal. ($C_{12}H_{13}BrN_2OS$ ⅓ $H_2O$) C, H, N.

EXAMPLE 20

6-p-Tolyl-imidazo[2,1-b]thiazole hydrobromide salt (27)

The title compound is prepared from 26 using a modification of method C with methoxyethanol instead of ethanol. The solvent was evaporated and the residue was recrystallized from ethanol in 49% yield: mp 260-262° C.; $^1$H-NMR (DMSO-d$_6$) 2.35 (s, 3H), 7.31 (d, 2H), 7.55 (d, 1H), 7.72 (d, 2H), 8.16 (d, 1H), 8.41 (s, 1H); Anal. ($C_{12}H_{11}BrN_2S$) C, H, N.

EXAMPLE 21

3-(2-oxo-2-p-tolylethyl)benzothiazol-2(3H)-one (28)

To a solution of 2-hydroxybenzothiazole (1.17 g, 7.58 mmol) in THF (10 mL) was added Et$_3$N (1.1 mL, 7.89 mmol). A solution of 2-bromo-4'-methylacetophenone (1.67 g, 7.06 mmol) in THf (10 mL) was added dropwise. Another equivalent of Et$_3$N was added after 24 hours. Purification by flash chromatography on silicagel (CH$_2$Cl$_2$) gave a white powder in 67% yield: mp 168-170° C.; $^1$H-NMR (DMSO-d$_6$) 2.43 (s, 3H), 5.62 (s, 2H), 7.21 (t, 1H), 7.27 (d, 1H) 7.32 (t, 1H), 7.42 (d, 2H), 7.70 (d, 1H), 8.01 (d, 2H); Anal. ($C_{16}H_{13}NO_2S$) C, H, N.

EXAMPLE 22

3-(2-oxo-2-p-tolylethyl)-4,5,6,7-tetrahydrobenzothiazol-2(3H)-one (29)

To a solution of 2-hydroxy-4,5,6,7-tetrahydrobenzothiazole (335 mg, 2.16 mmol) in DMF (3 mL) was added NaH (101 mg, 2.52 mmol). After stirring 10 minutes at room temperature, a solution of 2-bromo-4'-methylacetophenone (668 mg, 2.82 mmol) in DMF (5 mL) was added and the mixture was stirred overnight. Water was added and the mixture was extracted with EtOAc, dried over $MgSO_4$ and the solvent was evaporated. The oil recovered was purified by flash chromatography on silicagel ($CH_2Cl_2$) to give 29 as a solid in 65% yield: mp 108-110° C.; $^1$H-NMR (DMSO-$d_6$) 1.73 (s, 4H), 2.19 (s, 2H) 2.40 (m, 5H), 5.23 (s, 2H), 7.39 (d, 2H), 7.95 (d, 2H); Anal. ($C_{16}H_{17}NO_2S$) C, H, N.

EXAMPLE 23

N-(4-Methyl-benzylidene)-N'-quinazolin-4-yl-hydrazine (30)

A solution of quinazolin-4-yl-hydrazine (Gewald et al., *J. Prakt. Chem./Chem.-Ztg.* 1996, 338, 206-213) (265 mg, 1.65 mmol) was refluxed with tolualdehyde (400 µl, 3.39 mmol) in methanol for 1 hour. The solvent was evaporated and the resulting solid was triturated with water and filtered to give a yellow powder in 87% yield: mp 211-214° C.; $^1$H-NMR (DMSO-$d_6$) 2.37 (s, 3H), 7.29 (d, 2H), 7.47 (dt, 2H), 7.67 (t, 1H), 7.88 (d, 3H), 8.20 (m, 1H), 8.51 (s, 1H), 11.65 (s, 1H); HR-MS (EI) m/z 262.1223 ($M^+$).

EXAMPLE 24

Modulation of Proapoptotic Genes by Real Time PCR

Four proapoptotic genes were tested by real time PCR. Bax, PUMA (p53-upregulated modulator of apoptosis) and noxa are transcriptional targets of p53, proapoptotic members of the Bcl-2 family required to initiate apoptosis, Villunger et al., *Science* 2003, 302, 1036-1038. PUMA and noxa belong to the BH3-only protein subclass while Bax is a multidomain member of the family. DR5 (also called killer) is an apoptosis-inducing membrane receptor for tumor necrosis factor-related apoptosis-inducing ligand (also called TRAIL and Apo2 ligand). DR5 is a transcriptional target of p53, and its over expression induces cell death in vitro (Finnberg et al., *Molecular and Cellular Biology* 2005, 25, 2000-2013).

Figure 5:
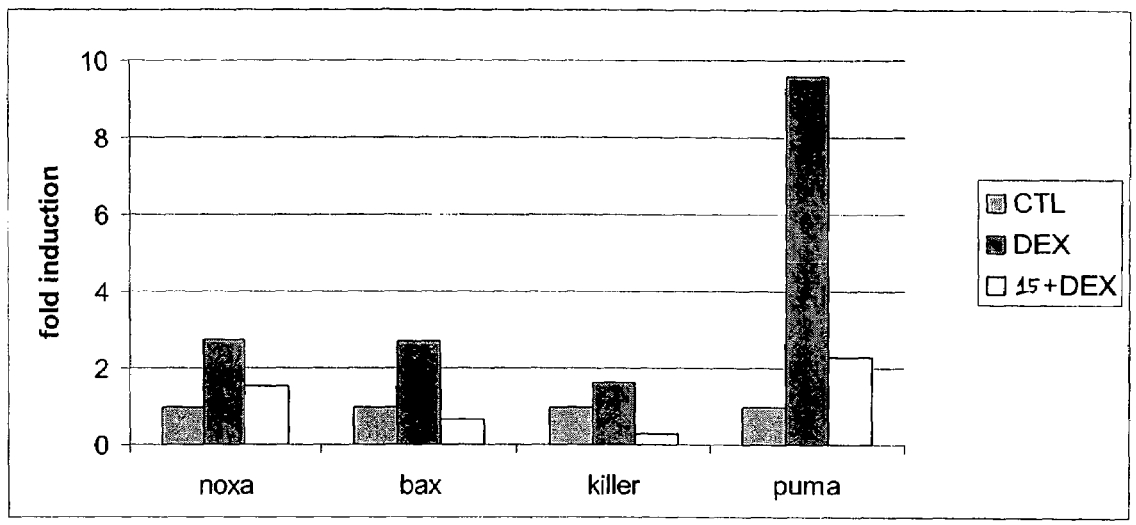
FIG. 5. shows the mRNA expression of apoptosis related genes in mouse thymocytes.

Upon treatment with DEX, all four genes were induced but only PUMA showed a significant increase of over 9-fold. Compound 15 was able to keep the level of the gene close to that of the control and even below it in the case of bax and killer (FIG. 5).

EXAMPLE 25

Modulation of PUMA Expression in Thymocytes Treated with DEX

Figure 6:
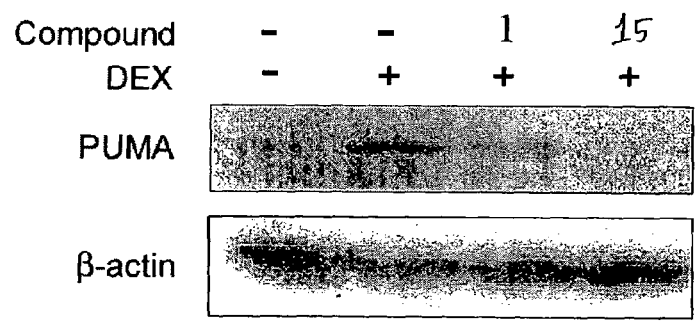
FIG. 6. shows the effect of compounds 1 and 15 on PUMA protein expression in mouse thymocytes. Thymocytes were pretreated with 10 μM of the indicated compounds and then exposed to 5 μM of dexamethasone for 6 hours. The cytosolic proteins were fractionated and then separated on a 4-12% gradient gel by SDS-PAGE and transferred to a PDVF membrane, which was probed with antibodies to PUMA and actin.

Confirmation of the induction of PUMA following DEX treatment and ensuing reduction in the presence of PFT-α was made using western blot analysis. PUMA expression was almost nonexistent in the control sample but was induced by DEX. Addition of 1 and 15 reduced the amount of protein induction. PFT-α provided only partial inhibition of PUMA but 15 again proved to be more effective than PFT-α resulting in a total inhibition of PUMA expression in mouse thymocytes. (FIG. 6).

EXAMPLE 26

Preparation of Pharmaceutical Dosage Forms

The following illustrate representative pharmaceutical dosage forms, containing a compound of formula (I), for therapeutic or prophylactic use in humans.

TABLE 4

| (i) | mg/tablet |
|---|---|
| Compound of Formula (I)-(V) | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

TABLE 5

| (ii) | mg/tablet |
|---|---|
| Compound of Formula (I)-(V) | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound of Formula (I)-(V) | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound of Formula (I)-(V) | 1.0 |
| Dibasic sodium phosphate | 12.0 |
| Monobasic sodium phosphate | 0.7 |
| Sodium chloride | 4.5 |
| 01 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound of Formula (I)-(V) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound of Formula (I)-(V) | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (IA):

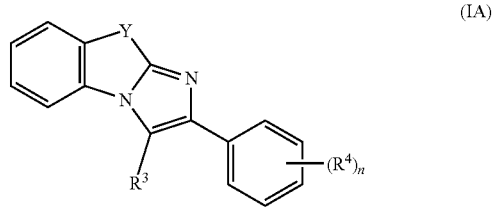

wherein $R^3$ is hydrogen, halo, hydroxy, cyano, —N($R^a$)($R^b$), —S($R^a$), —NO$_2$, (C$_1$-C$_6$)alkyl, (C$_1$-C$_6$)alkoxy, (C$_2$-C$_6$)alkynyl, (C$_2$-C$_6$)alkenyl, (C$_2$-C$_7$)alkanoyl, (C$_2$-C$_7$)alkanoyloxy, or (C$_3$-C$_7$)cycloalkyl, wherein $R^a$ and $R^b$ are each independently hydrogen, (C$_1$-C$_3$)alkyl, (C$_2$-C$_4$)alkanoyl, phenyl, benzyl, or phenethyl; or $R^a$ and $R^b$ together with the nitrogen to which they are attached are a 5-6 membered heterocyclic ring;

wherein $R^4$ is —N($R^a$)($R^b$) and wherein the —N($R^a$)($R^b$) of $R^4$ is a 5-6 membered heterocyclic ring, optionally comprising 1, 2, or 3 N($R^a$), non-peroxide O or S atoms;

Y is —S(O)$_{0-2}$; n is 1, 2, 3, 4, or 5; or a pharmaceutically acceptable salt thereof.

2. The compound of claim 1, wherein the —N($R^a$)($R^b$) of $R^4$ is pyrrolidino, piperidino or morpholino.

3. The compound of claim 2, wherein the —N($R^a$)($R^b$) of $R^4$ is pyrrolidino.

4. A method for protection of mammalian cells from the damaging effects of chemotherapy, or irradiation, comprising administering to a mammal in need of said protection an effective amount of a compound of claim 1.

* * * * *

UNITED STATES PATENT AND TRADEMARK OFFICE
CERTIFICATE OF CORRECTION

PATENT NO. : 7,601,846 B2
APPLICATION NO. : 11/271511
DATED : October 13, 2009
INVENTOR(S) : Howard B. Cottam et al.

It is certified that error appears in the above-identified patent and that said Letters Patent is hereby corrected as shown below:

In column 7, line 6, delete "$R^4$is" and insert -- $R^4$ is --, therefor.

In column 18, line 30, delete "Imnino" and insert -- Imino --, therefor.

In column 18, line 65, delete "(d, 1H) 7.32" and insert -- (d, 1H), 7.32 --, therefor.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,601,846 B2  Page 1 of 1
APPLICATION NO. : 11/271511
DATED : October 13, 2009
INVENTOR(S) : Cottam et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 886 days.

Signed and Sealed this

Fifth Day of October, 2010

David J. Kappos
*Director of the United States Patent and Trademark Office*